(12) United States Patent
Leonard et al.

(10) Patent No.: US 9,017,949 B2
(45) Date of Patent: Apr. 28, 2015

(54) METHOD OF SCREENING FOR COMPOUNDS USEFUL IN THE TREATMENT OF INSULIN RESISTANCE, IMPAIRED GLUCOSE TOLERANCE OR DIABETES

(75) Inventors: James N. Leonard, San Diego, CA (US); Yaron Hakak, San Diego, CA (US)

(73) Assignee: Arena Pharmacueticals, Inc., San Diego, CA (US)

( * ) Notice: Subject to any disclaimer, the term of this patent is extended or adjusted under 35 U.S.C. 154(b) by 1058 days.

(21) Appl. No.: 11/663,370

(22) PCT Filed: Sep. 21, 2005

(86) PCT No.: PCT/US2005/033795
§ 371 (c)(1),
(2), (4) Date: Oct. 8, 2009

(87) PCT Pub. No.: WO2006/036688
PCT Pub. Date: Apr. 6, 2006

(65) Prior Publication Data
US 2010/0093604 A1    Apr. 15, 2010

Related U.S. Application Data

(60) Provisional application No. 60/612,591, filed on Sep. 22, 2004.

(51) Int. Cl.
*G01N 33/566* (2006.01)
*G01N 33/68* (2006.01)

(52) U.S. Cl.
CPC .......... *G01N 33/566* (2013.01); *G01N 33/6845* (2013.01); *G01N 2500/00* (2013.01)

(58) Field of Classification Search
CPC ............ G01N 33/566; G01N 33/6845; G01N 2500/00
See application file for complete search history.

(56) References Cited

FOREIGN PATENT DOCUMENTS

| WO | 2003057730 | 7/2003 |
|---|---|---|
| WO | 2004038405 | 5/2004 |
| WO | WO2006102653 | 9/2006 |

OTHER PUBLICATIONS

Ge et al., "Activation of G Protein-Coupled Receptor 43 in Adipocytes Leads to Inhibition of Lipolysis and Suppression of Plasma Free Fatty Acids", Endocrinology (2008)149 (9): 4519-4526.
Karaki et al., "Short-chain fatty acid receptor, GPR43 is expressed by enteroendocrine cells and mucosal mast cells in rat intestine", Cell Tissue Res (2006) 324: 353-360.
Karaki et al., "Expression of the short-chain fatty acid receptor, GPR43, in the human colon", J Mol Hist (2008) 39:135-142.
Stoddart et al., "International Union of Pharmacology. LXXI. Free Fatty Acid Receptors FFA1, -2, and -3: Pharmacology and Pathophysiological Functions", Pharmacological Reviews (2008) vol. 60, No. 4, pp. 405-417.
Tazoe et al., "Roles of Short-Chain Fatty Acids Receptors, GPR41 and GPR43 on Colonic Functions", Journal of Physiology and Pharmacology (2008) 59, Suppl 2, 251-262.
Xiong et al., "Short-chain fatty acids stimulate leptin production in adipocytes through the G protein-coupled receptor GPR41"; PNAS, vol. 101, No. 4 pp. 1045-1050; Jan. 27, 2004.
Palczewski et al., "*Crystal structure of rhodopsin: A G protein-coupled receptor*", Science 2000 289:739-45.
Shin N et al., *Molecular modeling and site-specific mutagenesis of the histamine-binding site of the histamine H4 receptor.* Mol Pharmacol. 2002 62:38-47.
Chung DA et al., "*Mutagenesis and peptide analysis of the DRY motif in the alpha2A adrenergic receptor: evidence for alternate mechanisms in G protein-coupled receptor*" Biochem Biophys Res Commun. 2002 293:1233-41.
Mouledous et al., "*Functional inactivation of the nociceptin receptor by alanine substitution of glutamine 286 at the C terminus of transmembrane segment VI: evidence from a site-directed mutagenesis study of the ORL1 receptor transmembrane-binding domain*" Mol Pharmacol. 2000 57:495-502.
Krasnoperov et al., "*Structural requirements for alpha-latrotoxin binding and alpha-latrotoxin-stimulated secretion. A study with calcium-independent receptor of alpha-latrotoxin (CIRL) deletion mutants*" J Biol Chem. 1999 274:3590-6.
Hurley et al., "*Structure-function studies of the eighth hydrophobic domain of a serotonin receptor*" J Neurochem. 1999 72:413-21.
Akal-Strader et al., *Residues in the first extracellular loop of a G protein-coupled receptor play a role in signal transduction.* J Biol Chem. 2002 277:30581-90.
Yang et al., "*Molecular determinants of human melanocortin-4 receptor responsible for antagonist SHU9119 selective activity*" J Biol Chem. 2002 277:20328-35.
Ulloa-Aguirre et al., "*Structure-activity relationships of G protein-coupled receptors*" Arch Med Res. 1999 30:420-35 (Review).

(Continued)

*Primary Examiner* — Ruixiang Li
(74) *Attorney, Agent, or Firm* — James S. Keddie; Bozicevic, Field & Francis, LLP

(57) ABSTRACT

The present invention relates to a method for identifying a metabolic stabilizing compound by: a) contacting a candidate compound with GPR43, and b) determining whether GPR43 functionality is modulated, where a modulation in GPR43 functionality is indicative of the candidate compound being a metabolic stabilizing compound. In addition, the invention relates to a method for identifying a metabolic stabilizing compound, comprising: a) contacting a candidate compound with GPR43, and b) determining whether GPR43 functionality is increased, wherein an increase in GPR43 functionality is indicative of the candidate compound being a metabolic stabilizing compound. Further, the invention relates to a method for identifying a metabolic stabilizing compound, comprising: a) contacting a candidate compound with GPR43, and b) determining whether GPR43 functionality is decreased, wherein a decrease in GPR43 functionality is indicative of the candidate compound being a metabolic stabilizing compound.

4 Claims, 2 Drawing Sheets

(56) References Cited

OTHER PUBLICATIONS

Chollet et al., "*Biophysical approaches to G protein-coupled receptors: structure, function and dynamics*" J Comput Aided Mol Des. 1999 13:209-19 (Review).

Gimpl et al., "*The oxytocin receptor system: structure, function, and regulation,*" Physiol Rev. 2001 81:629-83 (Review).

Bai et al., "*Structure and function of the extracellular calcium-sensing receptor,*" Int J Mol Med. 1999 4:115-25 (Review).

Olah et al., "*The role of receptor structure in determining adenosine receptor activity,*" Pharmacol Ther. 2000 85:55-75 (Review).

Missale et al., "*Dopamine receptors: from structure to function,*" Physiol Rev. 1998 78:189-225 (Review).

Sealfon et al., *Functional domains of the gonadotropin-releasing hormone receptor*, Cell Mol Neurobiol. 1995 15:25-42 (Review).

Filizola et al., "*BUNDLE: a program for building the transmembrane domains of G-protein-coupled receptors,*" J Comput Aided Mol Des. 1998 12:111-8.

Orry et al., "*Modeling and docking the endothelin G-protein-coupled receptor,*" Biophys J. 2000 79:3083-94.

Califano, "*SPLASH: structural pattern localization analysis by sequential histograms,*" Bioinformatics. 2000 16:341-57.

Gouldson et al., "*Domain swapping in G-protein coupled receptor dimmers,*" Protein Eng. 1998 11:1181-93.

Gouldson et al., "Dimerization and domain swapping in G-protein-coupled receptors: a computational study," Neuropsychopharmacology. 2000 23:S60-77.

Ross et al., "*Development and comparison of two 3T3-L1 adipocyte models of insulin resistance: increased glucose flux vs glucosamine treatment,*" Biochemical and Biophysical Research Communications. 2000 273:1033-1041.

Knutson et al., "*Letter to the editor: 3T3-L1 adipocytes as a cell culture model of insulin resistance,*" In Vitro Cell. Dev. Biol.-Animal. Feb. 1997 33:77-81.

Pellicciari et al, "*Targeting TGR5 in diabesity: Focus on S-EMCA (INT-777) a potent and selective bile acid mimetic agonist,*" Division of Medicinal Chemistry Scientific Abstracts for the 239th National Meeting and Exposition, Mar. 21-25, 2010, San Francisco, California. Publication Date Feb. 22, 2010. Abstract #MEDI 314.

Tolhurst, et al., "Short-chain fatty acids stimulate glucagon-like peptide-1 secretion via the G-protein-coupled receptor FFAR2", Diabetes, 2012, 61:364-71.

Verspohl, "Recommended testing in diabetes research" Planta Med, 2002, 68:581-90.

Bjursell, et al., "Improved glucose control and reduced body fat mass in free fatty acid receptor 2-deficient mice fed a high-fat diet", Am J Physiol Endocrinol Metab, 300: E211-E220, 2011.

Swaminath, Gayathri, "Fatty acid binding receptors and their physiological role in type 2 diabetes", Arch. Pharm. Chem. Life Sci. 2008, 341, 753-761.

Tolhurst, et al., "Short-Chain Fatty Acids Stimulate Glucagon-Like Peptide-1 Secretion via the G-ProteinCoupled Receptor FFAR2", Diabetes. 2012, 61(2):364-71.

Kimura, et al. "The gut microbiota suppresses insulin-mediated fat accumulation via the short-chain fatty acid receptor GPR43", Nat Commun., 4:1829, pp. 1-12, 2013.

METHOD OF SCREENING FOR COMPOUNDS USEFUL IN THE TREATMENT OF INSULIN RESISTANCE, IMPAIRED GLUCOSE TOLERANCE OR DIABETES

FIELD OF THE INVENTION

The present invention relates to methods for identifying a metabolic stabilizing compound by determining whether a compound modulates GPR43 functionality. Accordingly, compounds of the present invention are useful in the prophylaxis or treatment of metabolic-related disorders such as hypoglycemia, aging, insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease.

BACKGROUND OF THE INVENTION

Cells use glucose as a main source of energy. Therefore, food is first broken down by the body to glucose prior to being utilized. Glucose is then released from the gut into the blood resulting in a rise in blood glucose levels. In response to this rise in glucose level, pancreatic β-islet cells increase their production and secretion of insulin. Insulin circulates through the blood and acts as a messenger, sending a signal to insulin responsive organs such as the adipose tissue, muscle and liver, to increase their intake of glucose. In this way a rise in blood glucose is accompanied by a subsequent increase in insulin secretion from β-cells. It is the rise in insulin that acts to return blood glucose levels to normal. In healthy individuals blood glucose levels are kept fairly constant. This state of equilibrium, called normoglycemia (normal glucose level) is tightly controlled by insulin.

In diseases such as diabetes this tight regulation of blood glucose level is lost, leading to the increased blood glucose levels observed in diabetics. A state of hyperglycemia (high glucose level) can occur due to an insufficient production of insulin by the pancreatic β-cells and/or through inadequate uptake of glucose by target organs such as muscle, liver and fat. The end result is an increase in blood glucose level. Thus, diabetes can be thought of as the result of two types of impairment impaired insulin secretion from the β-cells and impaired insulin sensitivity by the major insulin responsive organs. This impaired insulin sensitivity, also known as insulin resistance (because the organs are resistant to the effects of insulin), means that more insulin is required in order for the target organs to increase their glucose uptake. Insulin resistance leads to increased pressure on the β-cells because the β-cells need to increase their insulin secretion to compensate for insulin resistance. This is an escalating problem leading first to impaired glucose tolerance and; eventually, complete loss of insulin secretion due to the inability of the pancreas to keep up with the ever-increasing demand for insulin.

Diabetes is a diagnostic term for a group of disorders characterized by abnormal glucose homeostasis resulting in elevated blood glucose. There are many types of diabetes, but the two most common are Type I, also referred to as insulin-dependent diabetes mellitus or IDDM, and Type II, also referred to as non-insulin-dependent diabetes mellitus or NIDDM. Type I diabetes is mainly a disease with a young age of onset, and is due to the destruction of the insulin secreting β-cells in the pancreas by the immune system. In this case the body fails to recognize the pancreatic β-cells as being self and destroys its own cells. With the destruction of the β-cells there is a complete loss of insulin secretion and so affected individuals have an absolute dependency on insulin for survival. Type II diabetes is mainly a disease with a later age of onset, usually after the age of 40, but in recent years it is more common to find younger people being diagnosed with Type II diabetes. It is mainly characterized by insulin resistance and beta cell exhaustion and is often associated with obesity. Type II diabetes is more common than Type I diabetes and accounts for 90-95% of all diabetes cases diagnosed worldwide.

Chronic exposure of tissues to hyperglycemia can result in diverse complications including microvascular problems of neuropathy, retinopathy and nephropathy and the macrovascular complications of stroke, coronary heart disease, and peripheral vascular disease. Inappropriate control of blood glucose level is also a characteristic of diseases other than diabetes such as obesity and Syndrome X. For example, one of the characteristics of Syndrome X is insulin resistance or glucose intolerance. In addition, obesity is characterized by hyperinsulinemia and insulin resistance, a feature shared with NIDDM, hypertension and atherosclerosis. Further, obesity is a major risk factor for NIDDM. The risk of developing NIDDM is tripled in subjects 30% or more overweight, and three-quarters of NIDDM patients are overweight.

Obesity, which is the result of an imbalance between caloric intake and energy expenditure, is highly correlated with insulin resistance and diabetes in experimental animals and humans. However, the molecular mechanisms that are involved in obesity-diabetes syndromes still under investigation. During early development of obesity, increased insulin secretion balances insulin resistance and protects patients from hyperglycemia (Le Stunff, et al., *Diabetes* 43:696-702 (1989)). However, over time, β cell function deteriorates and non-insulin-dependent diabetes develops in about 20% of obese individuals (Pederson, P., *Diab. Metab. Rev.* 5:505-509 (1989), and Brancati, F. L., et al., *Arch. Intern. Med.* 159:957-963 (1999)). Given its high prevalence in modem societies, obesity has thus become the leading risk factor for NIDDM (Hill, J. O., et al., *Science* 280:1371-1374 (1998)). However, the factors which predispose some patients to alteration of insulin secretion in response to fat accumulation remain unknown. Unfortunately, effective long-term therapies to treat obesity are still not available.

Diabetes afflicts several million people worldwide. In the United States alone, there are more than 18 million diabetics, with 600,000 new cases diagnosed each year. People with diabetes are at higher risk for heart disease, blindness, kidney failure, infection, extremity amputations, and other conditions. It is estimated that the direct medical expenditures and indirect expenditures attributable to diabetes in the United States were $132 billion in 2002. Taken together, diabetes complications are one of the nation's leading causes of death.

Therapies do exist to treat diabetes, such as α-glucosidase inhibitors, biguanides, thiazolidinediones, meglitinides, sulfonylureas and exogenous insulin. However, these therapies have limited effectiveness and are associated with significant safety and tolerability issues such as risk for hypoglycemic episodes, weight gain, gastrointestinal disturbances and anemia. In addition, many of the treatment options require injection or multiple daily dosings which present compliance challenges.

Thus, there exists a need for the identification of an agent which safely and effectively treats a metabolic-related disorder such as, for example, diabetes, atherosclerosis and obesity. The present invention satisfies this need and provides related advantages as well.

SUMMARY OF THE INVENTION

Applicants have unexpectedly found that GPR43 is expressed in pancreatic islets and GPR43 is upregulated in db/db diabetic and ob/ob obese mice. In addition, Applicants disclose that GPR43 is highly induced in differentiated adipocytes. Further, Applicants disclose that inverse agonists or antagonists of GPR43 can be used to treat metabolic-related disorders such as insulin resistance, impaired glucose tolerance and diabetes.

In a first aspect, the invention features a method for identifying a metabolic stabilizing compound, comprising: a) contacting a candidate compound with GPR43, and b) determining whether GPR43 functionality is modulated, wherein a modulation in GPR43 functionality is indicative of the candidate compound being a metabolic stabilizing compound. In some embodiments, said GPR43 is human. In some embodiments, said determining comprises a second messenger assay.

In a second aspect, the invention features a metabolic stabilizing compound identified according to a method of the first aspect. In some embodiments, said metabolic stabilizing compound is a GPR43 agonist. In some embodiments, said metabolic stabilizing compound is a GPR43 inverse agonist or antagonist.

In a third aspect, the invention features a method for preparing a composition which comprises identifying a metabolic stabilizing compound and then admixing said compound with a carrier, wherein said compound is identified by a method of the first aspect.

In a fourth aspect, the invention features a pharmaceutical composition comprising, consisting essentially of, or consisting of a compound of the second aspect.

In a fifth aspect, the invention features a method for treating or preventing a metabolic-related disorder in an individual in need thereof, comprising administering to said individual an effective amount of a compound of the fourth aspect. In some embodiments, said metabolic-related disorder is hypoglycemia, aging, insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In some embodiments, a method of the fifth aspect further comprises administering to said individual an effective amount of an agent used for the treatment of diabetes, blood lipid disorders, or obesity in combination with an effective amount of a compound of the fourth aspect. In some embodiments, the individual is a mammal and in some embodiments the individual is a human.

In a sixth aspect, the invention features a method for the manufacture of a medicament comprising a compound of the fourth aspect for use as a metabolic stabilizing compound and a method for the manufacture of a medicament comprising a compound of the fourth aspect for use in the treatment of a metabolic-related disorder.

In a seventh aspect, the invention features a method for identifying a metabolic stabilizing compound, comprising: a) contacting a candidate compound with GPR43, and b) determining whether GPR43 functionality is decreased, wherein a decrease in GPR43 functionality is indicative of the candidate compound being a metabolic stabilizing compound. In some embodiments, said GPR43 is human. In some embodiments, said determining comprises a second messenger assay.

In an eighth aspect, the invention features a metabolic stabilizing compound identified according to a method of the seventh aspect. In some embodiments, said metabolic stabilizing compound is a GPR43 inverse agonist or antagonist.

In a ninth aspect, the invention features a method for preparing a composition which comprises identifying a metabolic stabilizing compound and then admixing said compound with a carrier, wherein said compound is identified by a method of the seventh aspect.

In a tenth aspect, the invention features a pharmaceutical composition comprising, consisting essentially of, or consisting of a compound of the eighth aspect.

In a eleventh aspect, the invention features a method for treating or preventing a metabolic-related disorder in an individual in need thereof, comprising administering to said individual an effective amount of a compound of the tenth aspect. In some embodiments, said metabolic-related disorder is insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In some embodiments, said metabolic-related disorder is insulin resistance, impaired glucose tolerance, or diabetes. In some embodiments, a method of the eleventh aspect further comprises administering to said individual an effective amount of an agent used for the treatment of diabetes, blood lipid disorders, or obesity in combination with an effective amount of a compound of the tenth aspect. In some embodiments, the individual is a mammal and in some embodiments the individual is a human.

In a twelfth aspect, the invention features a method for the manufacture of a medicament comprising a compound of the tenth aspect for use as a metabolic stabilizing compound and a method for the manufacture of a medicament comprising a compound of the tenth aspect for use in the treatment of a metabolic-related disorder.

In a thirteenth aspect, the invention features a method for treating or preventing a metabolic-related disorder, comprising administering to an individual in need thereof an effective amount of a GPR43 modulator. In some embodiments, said metabolic-related disorder is hypoglycemia or aging and said modulator is an agonist. In some embodiments, said metabolic-related disorder is insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease and said modulator is an inverse agonist or antagonist. In some embodiments, a method of the thirteenth aspect further comprises administering to said individual an effective amount of an agent used for the treatment of diabetes, blood lipid disorders, or obesity in combination with an effective amount of a GPR43 inverse agonist or antagonist. In some embodiments, said metabolic-related disorder is insulin resistance, impaired glucose tolerance, or diabetes.

In a fourteenth aspect, the invention features a method for treating or preventing a disorder treatable or preventable by decreasing GPR43 function, comprising administering to an individual in need thereof an effective amount of a GPR43 inverse agonist or antagonist. In some embodiments, said disorder is a metabolic-related disorder, for example, insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In some embodiments, said metabolic-related disorder is insulin resistance, impaired glucose tolerance, or diabetes. In some embodiments, said metabolic-related disorder is Type II diabetes. In some embodiments, a method of the fourteenth aspect further comprises administering to said individual an effective amount of an agent used for the treatment of diabetes, blood lipid disorders, or obesity in combination with an effective amount of a GPR43 inverse agonist or antagonist.

DETAILED DESCRIPTION

Figure 1:
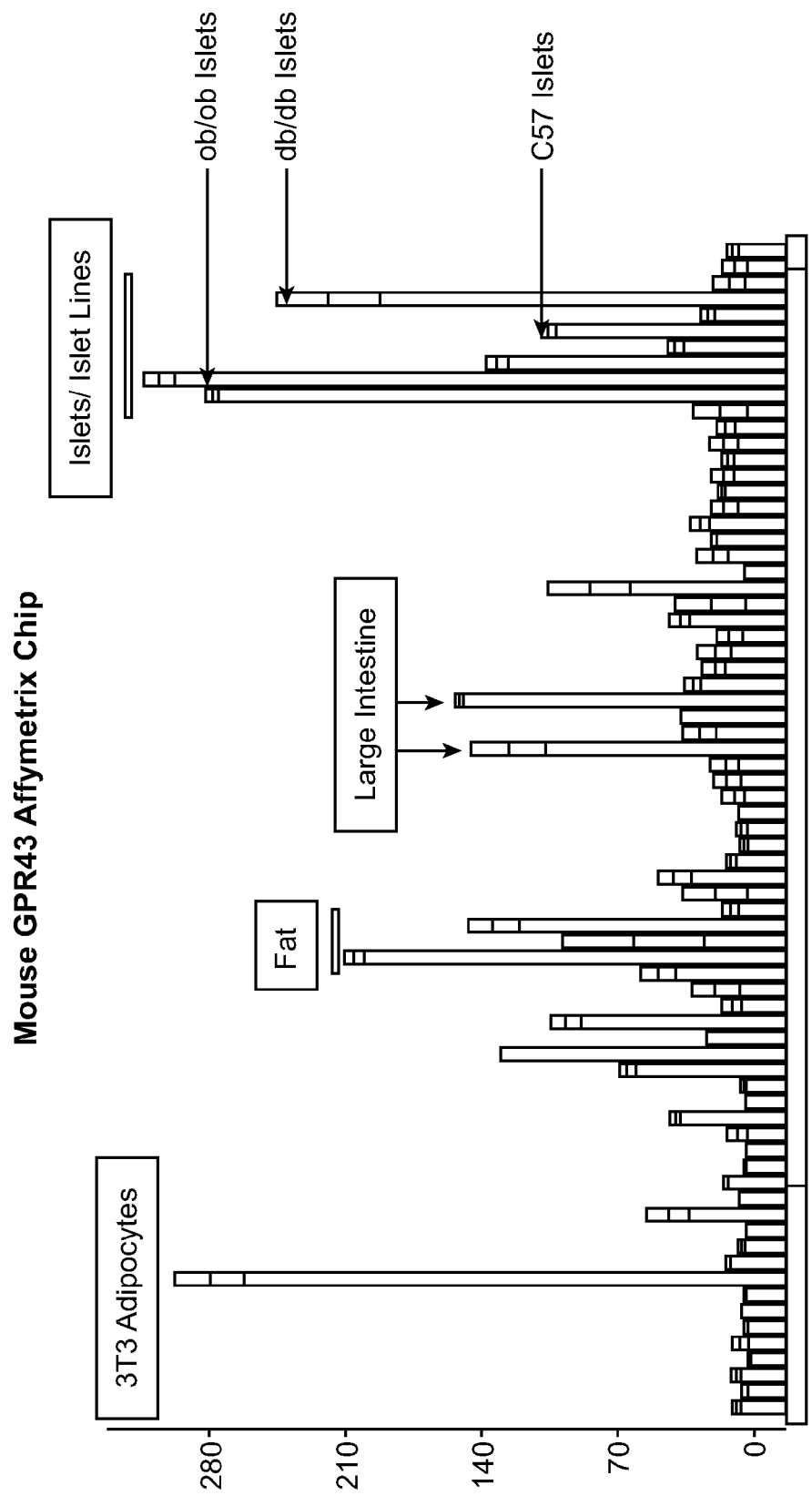
FIG. 1 shows Affymetrix gene chip analysis of mouse GPR43 expression in mouse adult and fetal tissues and cells.

Applicants have disclosed herein that mouse GPR43 is highly expressed in fat, large intestine, and pancreatic islet cells (see FIG. 1) and mouse GPR43 is up-regulated in pancreatic islets isolated from db/db diabetic and ob/ob obese mice compared to pancreatic islets from wild-type mice (see FIG. 1). In addition, Applicants have disclosed herein that mouse GPR43 is highly induced in differentiated 3T3-L1 adipocytes (see FIG. 1). Further, Applicants have disclosed that human GPR43 is expressed in several tissues including pancreas (see FIG. 2, upper panel) and mouse GPR43 is expressed in several tissues and in pancreatic islet cell lines (see FIG. 2, lower panel).

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs. GPCRs represent an important area for the development of pharmaceutical products: from approximately 20 of the 100 known GPCRs, approximately 60% of all prescription pharmaceuticals have been developed.

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor); there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

There are also promiscuous G proteins, which appear to couple to several classes of GPCRs to the phospholipase C pathway, such as $G\alpha15$ or $G\alpha16$ (Offermanns & Simon, *J Biol Chem* 270:15175-80 (1995)), or chimeric G proteins designed to couple a large number of different GPCRs to the same pathway, e.g. phospholipase C (Milligan & Rees, *Trends in Pharmaceutical Sciences* 20:118-24 (1999)).

Gi-coupled GPCRs lower intracellular cAMP levels. The melanophore technology (see infra) is useful for identifying Gi-coupled GPCRs and also for identifying modulators of said Gi-coupled GPCRs.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor can be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

The sequence of GPR43 was first published in the literature by Sawzdargo et al. (Sawzdargo et al., *Biochem. Biophys. Res. Commun.*, 239:543-547 (1997)). Sawzdargo et al. amplified human genomic DNA using PCR with degenerate primers based on conserved sequences within the human and rat galanin receptor 1 (GALR1) and rat GALR2. One product contained a segment showing 100% homology to a portion of the 3-prime region of the human CD22 gene. The authors identified a PAC clone in the sequence databases that overlaps this region and contains a novel GPCR gene, GPR43. The intronless GPR43 gene is located approximately 77 kb downstream of the GPR42 gene. GPR43 encodes a deduced 330 amino acid protein with 7 transmembrane domains. The GPR43 protein shares 28% amino acid identity with GPR40, but little similarity with GALRs. In addition, GPR43 shares 43% amino acid identity with GPR41. A third family member, GPR42, is most likely a recent gene duplication of GPR41 and may be a pseudogene.

GPR43 was classified as an orphan receptor, meaning that no ligand had been identified for the receptor. Recently, Brown et al. have reported that GPR43 is activated by acetate and other short chain carboxylic acid anions (Brown et al., *J. Biol. Chem.*, 278:11312-11319 (2003)). In addition, Brown et al. indicate that GPR43 activates the $G_i$, $G_q$ and $G_{12}$ families of G proteins. Further, Brown et al. report that GPR43 is found at highest levels in immune cells such as neutrophils and monocytes.

DEFINITIONS

The scientific literature that has evolved around receptors has adopted a number of terms to refer to ligands having various effects on receptors. For clarity and consistency, the following definitions will be used throughout this patent document.

AGONIST shall mean material, for example, a ligand or candidate compound, that activates an intracellular response when it binds to the receptor. An intracellular response can be, for example, enhancement of GTP binding to membranes or modulation of the level of a second messenger such as cAMP or IP3. In some embodiments, an AGONIST is material not previously known to activate the intracellular response when it binds to the receptor (for example, to enhance GTPγS binding to membranes or to lower intracellular cAMP level). In some embodiments, an AGONIST is material not previously known to decrease blood glucose level when it binds to the receptor. The term AGONIST also includes PARTIAL AGONISTS which are materials, for example, ligands or candidate compounds, which activate the intracellular response when they bind to the receptor to a lesser degree or extent than do full agonists.

ANTAGONIST shall mean material, for example, ligands or candidate compounds that competitively bind to the receptor at the same site as an agonist but which does not activate an intracellular response, and can thereby inhibit an intracellular response elicited by the agonist. An ANTAGONIST does not diminish the baseline intracellular response in the absence of an agonist. In some embodiments, an ANTAGONIST is material not previously known to compete with an agonist to inhibit a cellular response when it binds to the receptor (for example, wherein the cellular response is GTPγS binding to membranes or to the lowering of intracellular cAMP level).

ANTIBODY is intended herein to encompass monoclonal antibodies and polyclonal antibodies. The term ANTIBODY is further intended to encompass IgG, IgA, IgD, IgE, and IgM. Antibodies include whole antibodies, including single-chain whole antibodies, and antigen binding fragments thereof, including Fab, Fab', F(ab)2 and F(ab')2. Antibodies can be from any natural or synthetic origin, for example, from human, murine, rabbit, goat, guinea pig, hamster, camel, donkey, sheep, horse or chicken. Antibodies can have binding affinities with a dissociation constant or Kd value, for example, less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M $10^{-14}$M, $5\times10^{-15}$M and $10^{-15}$M. Antibodies of the present invention can be prepared by any suitable method known in the art.

CANDIDATE COMPOUND shall mean a molecule (for example, a chemical compound) that is amenable to a screening technique. The term candidate compound specifically excludes any compound already known to modulate GPR43, for example, a known agonist of GPR43.

COMPOSITION shall mean a material comprising at least two compounds or two components; for example, a "pharmaceutical composition" is a composition.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

DIABETES as used herein is intended to encompass the usual diagnosis of diabetes made from any method including, for example, the following list: symptoms of diabetes (e.g., polyuria, polydipsia, polyphagia) plus casual blood glucose levels of greater than or equal to 200 mg/dl, wherein casual blood glucose is defined any time of the day regardless of the timing of meal or drink consumption; or 8 hour fasting blood glucose levels of greater than or equal to 126 mg/dl; or blood glucose levels of greater than or equal to 200 mg/dl two hours following oral administration of 75 g anhydrous glucose dissolved in water. In addition, the term diabetes as used herein also includes the "pre-diabetic" state as defined by the American Diabetes Association to be a fasting blood glucose level of 100-125 mg/dl or blood glucose levels of 140-199 mg/dl two hours following oral administration of glucose. Diabetes can be precipitated by several conditions including, for example, autoimmune destruction of beta islet cells, beta cell apoptosis, or pregnancy (gestational diabetes).

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus. In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor can be in reference to an in vitro screening system.

EFFECTIVE AMOUNT means an amount of active compound or pharmaceutical composition that elicits the desired biological or medicinal response in a tissue, system, or individual that is being sought by the researcher or medical doctor or other clinician. For example, an effective dose can be an amount that can treat a metabolic-related disorder. Also, for example, an effective dose can be an amount that can prevent a metabolic-related disorder.

IMPAIRED GLUCOSE TOLERANCE (IGT) as used herein is intended to indicate that condition associated with insulin-resistance that is intermediate between frank, type 2 diabetes and normal glucose tolerance (NGT). IGT is diagnosed by a procedure wherein an affected person's postprandial glucose response is determined to be abnormal as assessed by 2-hour postprandial plasma glucose levels. In this test, a measured amount of glucose is given to the patient and blood glucose levels are measured at regular intervals, usually every half hour for the first two hours and every hour thereafter. In a "normal" or non-IGT individual, glucose levels rise during the first two hours to a level less than 140 mg/dl and then drop rapidly. In an IGT individual, the blood glucose levels are higher and the drop-off level is at a slower rate.

IN NEED OF PREVENTION OR TREATMENT as used herein refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that include the knowledge that the individual or animal is ill, or will be ill, as the result of a condition that is treatable by the compounds of the invention.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is a good correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

INVERSE AGONIST means material, for example, a ligand or candidate compound that binds either to the endogenous form or to the constitutively activated form of the receptor so as to reduce the baseline intracellular response of the receptor observed in the absence of an agonist. An intracellular response can be, for example, modulation of GTP binding to membranes or modulation of the level of a second messenger such as cAMP or IP3. In some embodiments, an INVERSE AGONIST is material not previously known to reduce the baseline intracellular response of the receptor observed in the absence of an agonist.

LIGAND shall mean an endogenous, naturally occurring molecule specific for an endogenous, naturally occurring receptor.

METABOLIC-RELATED DISORDER means a disorder of metabolism. As used herein a metabolic-related disorder is intended herein to include, for example, hypoglycemia, aging, insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease.

METABOLIC-STABILIZING COMPOUND is intended to mean a compound that stabilizes a metabolic parameter. Metabolic parameters include any measure of metabolism such as the level of lipids, sugars, enzymes or other proteins in response to metabolic processes. For example, a metabolic-stabilizing compound can stabilize blood glucose levels in an individual.

As used herein, the terms MODULATE or MODULATING shall mean to refer to an increase or decrease in the amount, quality, response or effect of a particular activity, function or molecule. A GPR43 MODULATOR is an agent that modulates the GPR43 receptor.

PHARMACEUTICAL COMPOSITION shall mean a composition comprising at least one compound and a pharmaceutically acceptable carrier. For example, a pharmaceutical composition can comprise at least one active ingredient, whereby the composition is amenable to investigation for a specified, efficacious outcome in an animal (for example, a mammal such as a human). Those of ordinary skill in the art will understand and appreciate the techniques appropriate for determining whether an active ingredient has a desired efficacious outcome based upon the needs of the artisan.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins. A GPR43 functionality can be, for example, binding a G-protein such as Gi, Gq or G12, signaling through a second messenger such as cAMP, IP3 or calcium, binding to a GPR43-specific antibody, or binding to a compound such as a GPR43 agonist.

SECOND MESSENGER shall mean an intracellular response produced as a result of receptor activation. A second messenger can include, for example, inositol triphosphate (IP3), diacylglycerol (DAG), cyclic AMP (cAMP), cyclic GMP (cGMP), and Ca2+. Second messenger response can be measured for a determination of receptor activation. In addition, second messenger response can be measured for the direct identification of candidate compounds, including for example, inverse agonists, partial agonists, agonists, and antagonists.

The invention provides a method for identifying a metabolic stabilizing compound, comprising: a) contacting a candidate compound with GPR43, and b) determining whether GPR43 functionality is modulated, wherein a modulation in GPR43 functionality is indicative of the candidate compound being a metabolic stabilizing compound.

As used herein, "GPR43" refers to a polypeptide with the amino acid sequence as shown in SEQ ID NO:2, or a variant or ortholog of this sequence that retains substantially the function of a polypeptide with the amino acid sequence as referenced in SEQ ID NO:2.

It is understood that limited variations or modifications to GPR43 can be made without destroying its function. For example, GPR43 is intended to include other GPR43 polypeptides, for example, mammalian species orthologs of the human GPR43 polypeptide. The nucleotide and amino acid sequences of species orthologs of human GPR43 are present in the database, for example, a mouse ortholog of GPR43 can be found in GenBank at Accession No. NM_146187 and a rat ortholog of GPR43 can be found in GenBank at Accession No. AB106675. In addition, GPR43 includes variants such as allelic variants, splice variants and conservative amino acid substitution variants of GPR43. For example, GPR43 includes variants that retain substantially the function of the wild-type GPR43 polypeptide such as, for example, the ability to signal through G-alpha i, G-alpha q or G-alpha 12, the ability to bind to a GPR43-specific antibody, or the ability to bind to a compound such as a known ligand or agonist. A GPR43 variant need not function to the same level as the wild-type GPR43, and need not contain every function of the wild-type GPR43.

Conservative and non-conservative amino acid changes, gaps, and insertions to an amino acid sequence can be compared to a reference sequence using available algorithms and programs such as the Basic Local Alignment Search Tool ("BLAST") using default settings [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402].

It is understood that a fragment of GPR43 which retains substantially a function of the entire polypeptide is included in the definition. For example, a signal generating domain of GPR43 or a compound binding domain of GPR43 can be used in lieu of the entire polypeptide. In addition, GPR43 can contain heterologous sequences such as an epitope tag or other fused polypeptide. Further, GPR43 can contain a label, for example, a radiolabel, fluorescent label or enzymatic label.

In one embodiment, the methods of the invention can be applied using a polypeptide comprising 99%, 98%, 95%, 92%, 90%, 85%, 80%, or 75% sequence identity to SEQ ID NO:2.

In some embodiments, said variant of GPR43 is a non-endogenous, constitutively activated mutant of GPR43. In one embodiment, said GPR43 is derived from a mammal. In another embodiment, said GPR43 is human.

In certain embodiments, said GPR43 is recombinant. In certain embodiments, said contacting comprises contacting with a host cell or with membrane of a host cell that expresses the GPCR, wherein the host cell comprises an expression vector comprising a polynucleotide encoding the receptor. In some embodiments, said contacting is carried out in the presence of a known agonist of the GPCR.

In certain embodiments, said method further comprises the step of comparing the modulation of the receptor caused by the candidate compound to a second modulation of the receptor caused by contacting the receptor with a known modulator of the receptor. In certain embodiments, said known modulator is an agonist.

In some embodiments, said metabolic stabilizing compound is a blood glucose stabilizing compound. In some embodiments, said metabolic stabilizing compound is an insulin secretion modulator.

In some embodiments, said determining comprises a second messenger assay, for example, determining is through the measurement of GTPγS binding to membrane comprising said GPCR. In certain embodiments, said GTPγS is labeled with [$^{35}$S]. In certain embodiments, said determining is through the measurement of the level of a second messenger selected from the group consisting of cyclic AMP (cAMP), cyclic GMP (cGMP), inositol triphosphate (IP3), diacylglycerol (DAG), MAP kinase activity, and calcium ($Ca^{2+}$). In certain embodiments, said second messenger is cAMP. In certain embodiments, said measurement of cAMP is carried out using whole-cell adenylyl cyclase assay. In certain embodiments, said measurement of cAMP is carried out with membrane comprising said GPCR. In certain embodiments, said determining is through measurement of intracellular IP3. In certain embodiments, said second messenger is MAP kinase activity. In some embodiments, said determining is through CRE-reporter assay. In certain embodiments, said reporter is luciferase. In some embodiments, said reporter is β-galactosidase. In certain embodiments, said determining or said comparing is through measurement of intracellular calcium ($Ca^{2+}$), for example, using a FLIPR assay.

In some embodiments, said determining is through measurement of glucose uptake by adipocytes obtained from a mammal.

In certain embodiments, said determining is through the use of a melanophore assay.

In the methods of the invention, control reactions can be performed to show specificity of the response. For example, mock-transfected cells can be compared to GPR43 transfected cells to show specificity of a response to the GPR43 receptor.

In the methods of the invention, in certain embodiments, said candidate compound is not an antibody or antigen-binding derivative thereof. In certain embodiments, said candidate compound is not a peptide. In certain embodiments, said candidate compound is not a polypeptide.

As stated above, receptor functionality refers to the normal operation of a receptor to receive a stimulus and moderate an effect in the cell, including, but not limited to regulating gene transcription, regulating the influx or efflux of ions, effecting a catalytic reaction, and/or modulating activity through G-proteins. A GPR43 functionality can be, for example, binding a G-protein such as Gi, Gq or G12, signaling through a second messenger such as cAMP, IP3, or calcium, binding to a GPR43-specific antibody, or binding to a compound such as a GPR43 agonist.

In the methods of the invention, determining can comprise a second messenger assay. The initiation of an intracellular signal can be determined, for example, through the measurement of the level of a second messenger such as cyclic AMP (cAMP), cyclic GMP (cGMP), inositol triphosphate (IP3), diacylglycerol (DAG), MAP kinase, or calcium. Several assays are well known in the art for measuring these second messengers, for example, cAMP assays, IP3 assays, the FLIPR assay, the melanophore assay, or CRE-reporter assay. In addition, examples of second messenger assays are disclosed herein in Examples 6-11. In certain embodiments, said second messenger is cAMP. In other embodiments, said second messenger is IP3. In further embodiments said second messenger is calcium.

In one embodiment, said determining is through the measurement of GTPγS binding to membrane comprising said GPCR. Such assays are well known in the art and exemplified herein in Examples 6 and 8. In certain embodiments, said GTPγS is labeled with [$^{35}$S].

The invention also relates to a metabolic stabilizing compound identifiable according to the method of: a) contacting a candidate compound with GPR43, and b) determining whether GPR43 functionality is modulated, wherein a modulation in GPR43 functionality is indicative of the candidate compound being a metabolic stabilizing compound.

For example, the invention provides a metabolic stabilizing compound identified according to the method of: a) contacting a candidate compound with GPR43, and b) determining whether GPR43 functionality is modulated, wherein a modulation in GPR43 functionality is indicative of the candidate compound being a metabolic stabilizing compound.

In one embodiment, said metabolic stabilizing compound is a GPR43 agonist. In some embodiments, said agonist is material not previously known to activate an intracellular response when it binds to the GPR43 receptor.

In some embodiments, said metabolic stabilizing compound is a GPR43 agonist with an EC50 of less than 10 μM, of less than 1 μM, of less than 100 μM, or of less than 10 nM. In some embodiments, said metabolic stabilizing compound is an agonist with an EC50 of a value selected from the interval of 1 nM to 10 μM. In some embodiments, said metabolic stabilizing compound is an agonist with an EC50 of a value selected from the interval of 1 nM to 1 μM. In some embodiments, said metabolic stabilizing compound is an agonist with an EC50 of a value selected from the interval of 1 nM to 100 nM. In some embodiments, said metabolic stabilizing compound is an agonist with an EC50 of a value selected from the interval of 1 nM to 10 nM.

In certain embodiments, said EC50 is determined using an assay selected from the group consisting of: IN assay carried out using transfected HEK293 cells expressing recombinant GPR43 polypeptide; and melanophore assay carried out using transfected melanophores expressing recombinant GPR 43 polypeptide. In some embodiments, said metabolic stabilizing compound is an agonist with an EC50 of less than 10 μM, of less than 1 μM, of less than 100 nM, or of less than 10 nM in said assay. In some embodiments, said metabolic stabilizing compound is an agonist with an EC50 of less than 10 μM in said assay. In some embodiments, said metabolic stabilizing compound is an agonist with an EC50 of less than 9 μM in said assay. In some embodiments, said metabolic stabilizing compound is an inverse agonist or antagonist with an EC50 of less than 8 µM in said assay. In some embodiments, said metabolic stabilizing compound is an agonist with an EC50 of less than 7 µM in said assay. In some embodiments, said metabolic stabilizing compound is an agonist with an EC50 of less than 6 µM in said assay. In some embodiments, said metabolic stabilizing compound is an agonist with an EC50 of less than 5 µM in said assay. In some embodiments, said metabolic stabilizing compound is an agonist with an EC50 of less than 4 µM in said assay. In some embodiments, said metabolic stabilizing compound is an agonist with an EC50 of less than 3 µM in said assay. In some embodiments, said metabolic stabilizing compound is an agonist with an EC50 of less than 2 µM in said assay. In some embodiments, said metabolic stabilizing compound is an agonist with an EC50 of less than 1 µM in said assay. In some embodiments, said metabolic stabilizing compound is an agonist with an EC50 of less than 900 nM in said assay. In some embodiments, said metabolic stabilizing compound is an agonist with an EC50 of less than 800 nM in said assay. In some embodiments, said metabolic stabilizing compound is an agonist with an EC50 of less than 700 nM in said assay. In some embodiments, said metabolic stabilizing compound is an agonist with an EC50 of less than 600 nM in said assay. In some embodiments, said metabolic stabilizing compound is an agonist with an EC50 of less than 500 nM in said assay. In some embodiments, said metabolic stabilizing compound is an agonist with an EC50 of less than 400 nM in said assay. In some embodiments, said metabolic stabilizing compound is an agonist with an EC50 of less than 300 nM in said assay. In some embodiments, said metabolic stabilizing compound is an agonist with an EC50 of less than 200 nM in said assay. In some embodiments, said metabolic stabilizing compound is an agonist with an EC50 of less than 100 nM in said assay. In some embodiments, said metabolic stabilizing compound is an agonist with an EC50 of less than 90 nM in said assay. In some embodiments, said metabolic stabilizing compound is an agonist with an EC50 of less than 80 nM in said assay. In some embodiments, said metabolic stabilizing compound is an agonist with an EC50 of less than 70 nM in said assay. In some embodiments, said metabolic stabilizing compound is an agonist with an EC50 of less than 60 nM in said assay. In some embodiments, said metabolic stabilizing compound is an agonist with an EC50 of less than 50 nM in said assay. In some embodiments, said metabolic stabilizing compound is an agonist with an EC50 of less than 40 nM n said assay. In some embodiments, said metabolic stabilizing compound is an agonist with an EC50 of less than 30 nM in said assay. In some embodiments, said metabolic stabilizing compound is an agonist with an EC50 of less than 20 nM in said assay. In some embodiments, said metabolic stabilizing compound is an agonist with an EC50 of less than 10 nM in said assay. In some embodiments, said metabolic stabilizing compound is an agonist with an EC50 in said assay of a value selected from the interval of 1 nM to 10 µM. In some embodiments, said metabolic stabilizing compound is an agonist with an EC50 in said assay of a value selected from the interval of 1 nM to 1 µM. In some embodiments, said metabolic stabilizing compound is an agonist with an EC50 in said assay of a value selected from the interval of 1 nM to 100 nM. In some embodiments, said metabolic stabilizing compound is an agonist with an EC50 in said assay of a value selected from the interval of 1 nM to 10 nM. In some embodiments, said metabolic stabilizing compound is selective for the GPCR.

In some embodiments, said metabolic stabilizing compound is a GPR43 inverse agonist or antagonist. In some embodiments, said metabolic stabilizing compound is a GPR43 inverse agonist or antagonist with an IC50 of less than 10 µM, of less than 1 µM, of less than 100 nM, or of less than 10 nM. In some embodiments, said metabolic stabilizing compound is an inverse agonist or antagonist with an IC50 of a value selected from the interval of 1 nM to 10 µM. In some embodiments, said metabolic stabilizing compound is an inverse agonist or antagonist with an IC50 of a value selected from the interval of 1 nM to 1 µM. In some embodiments, said metabolic stabilizing compound is an inverse agonist or antagonist with an IC50 of a value selected from the interval of 1 nM to 100 nM. In some embodiments, said metabolic stabilizing compound is an inverse agonist or antagonist with an IC50 of a value selected from the interval of 1 nM to 10 nM.

In certain embodiments, said IC50 is determined using an assay selected from the group consisting of: IP3 assay carried out using transfected HEK293 cells expressing recombinant GPR43 polypeptide; and melanophore assay carried out using transfected melanophores expressing recombinant GPR43 polypeptide. In some embodiments, said metabolic stabilizing compound is an inverse agonist or antagonist with an IC50 of less than 10 µM, of less than 1 µM, of less than 100 nM, or of less than 10 nM in said assay. In some embodiments, said metabolic stabilizing compound is an inverse agonist or antagonist with an IC50 of less than 10 µM in said assay. In some embodiments, said metabolic stabilizing compound is an inverse agonist or antagonist with an IC50 of less than 9 µM in said assay. In some embodiments, said metabolic stabilizing compound is an inverse inverse agonist or antagonist or antinverse agonist or antagonist with an IC50 of less than 8 µM in said assay. In some embodiments, said metabolic stabilizing compound is an inverse agonist or antagonist with an IC50 of less than 7 µM in said assay. In some embodiments, said metabolic stabilizing compound is an inverse agonist or antagonist with an IC50 of less than 6 µM in said assay. In some embodiments, said metabolic stabilizing compound is an inverse agonist or antagonist with an IC50 of less than 5 µM in said assay. In some embodiments, said metabolic stabilizing compound is an inverse agonist or antagonist with an IC50 of less than 4 µM in said assay. In some embodiments, said metabolic stabilizing compound is an inverse agonist or antagonist with an IC50 of less than 3 µM in said assay. In some embodiments, said metabolic stabilizing compound is an inverse agonist or antagonist with an IC50 of less than 2 µM in said assay. In some embodiments, said metabolic stabilizing compound is an inverse agonist or antagonist with an IC50 of less than 1 µM in said assay. In some embodiments, said metabolic stabilizing compound is an inverse agonist or antagonist with an IC50 of less than 900 nM in said assay. In some embodiments, said metabolic stabilizing compound is an inverse agonist or antagonist with an IC50 of less than 800 nM in said assay. In some embodiments, said metabolic stabilizing compound is an inverse agonist or antagonist with an IC50 of less than 700 nM in said assay. In some embodiments, said metabolic stabilizing compound is an inverse agonist or antagonist with an IC50 of less than 600 nM in said assay. In some embodiments, said metabolic stabilizing compound is an inverse agonist or antagonist with an IC50 of less than 500 nM in said assay. In some embodiments, said metabolic stabilizing compound is an inverse agonist or antagonist with an IC50 of less than 400 nM n said assay. In some embodiments, said metabolic stabilizing compound is an inverse agonist or antagonist with an IC50 of less than 300 nM in said assay. In some embodiments, said metabolic stabilizing compound is an inverse agonist or antagonist with an IC50 of less than 200 nM in said assay. In some embodiments, said metabolic stabilizing compound is an inverse agonist or antagonist with an IC50 of less than 100 nM in said assay. In some embodiments, said metabolic stabilizing compound is an inverse agonist or antagonist with an IC50 of less than 90 nM in said assay. In some embodiments, said metabolic stabilizing compound is an inverse agonist or antagonist with an IC50 of less than 80 nM in said assay. In some embodiments, said metabolic stabilizing compound is an inverse agonist or antagonist with an IC50 of less than 70 nM in said assay. In some embodiments, said metabolic stabilizing compound is an inverse agonist or antagonist with an IC50 of less than 60 nM in said assay. In some embodiments, said metabolic stabilizing compound is an inverse agonist or antagonist with an IC50 of less than 50 nM in said assay. In some embodiments, said metabolic stabilizing compound is an inverse agonist or antagonist with an IC50 of less than 40 nM n said assay. In some embodiments, said metabolic stabilizing compound is an inverse agonist or antagonist with an IC50 of less than 30 nM in said assay. In some embodiments, said metabolic stabilizing compound is an inverse agonist or antagonist with an IC50 of less than 20 nM in said assay. In some embodiments, said metabolic stabilizing compound is an inverse agonist or antagonist with an IC50 of less than 10 nM in said assay. In some embodiments, said metabolic stabilizing compound is an inverse agonist or antagonist with an IC50 in said assay of a value selected from the interval of 1 nM to 10 μM. In some embodiments, said metabolic stabilizing compound is an inverse agonist or antagonist with an IC50 in said assay of a value selected from the interval of 1 nM to 1 μM. In some embodiments, said metabolic stabilizing compound is an inverse agonist or antagonist with an IC50 in said assay of a value selected from the interval of 1 nM to 100 nM. In some embodiments, said metabolic stabilizing compound is an inverse agonist or antagonist with an IC50 in said assay of a value selected from the interval of 1 nM to 10 nM. In some embodiments, said metabolic stabilizing compound is selective for the GPCR.

In some embodiments, said metabolic stabilizing compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said orally bioavailable metabolic stabilizing compound is further able to cross the blood-brain bather.

In addition, the invention provides a method for preparing a composition which comprises identifying a metabolic stabilizing compound and then admixing said compound with a carrier, wherein said compound is identifiable by the method of: a) contacting a candidate compound with GPR43, and b) determining whether GPR43 functionality is modulated, wherein a modulation in GPR43 functionality is indicative of the candidate compound being a metabolic stabilizing compound. For example, the invention provides a method for preparing a composition which comprises identifying a metabolic stabilizing compound and then admixing said compound with a carrier, wherein said compound is identified by the method of: a) contacting a candidate compound with GPR43, and b) determining whether GPR43 functionality is modulated, wherein a modulation in GPR43 functionality is indicative of the candidate compound being a metabolic stabilizing compound.

The invention also provides a pharmaceutical composition comprising, consisting essentially of, or consisting of the metabolic stabilizing compound identified according to the method of: a) contacting a candidate compound with GPR43, and b) determining whether GPR43 functionality is modulated, wherein a modulation in GPR43 functionality is indicative of the candidate compound being a metabolic stabilizing compound.

A compound can be formulated into pharmaceutical compositions using techniques well known to those in the art. Suitable pharmaceutically-acceptable carriers, outside those mentioned herein, are available to those in the art; for example, see Remington's Pharmaceutical Sciences, 16$^{th}$ Edition, 1980, Mack Publishing Co., (Oslo et al., eds.).

While it is possible that, for use in the prophylaxis or treatment, a compound identified by methods of the invention can in an alternative use be administered as a raw or pure chemical, it can be useful to present the compound or active ingredient as a pharmaceutical formulation or composition further comprising a pharmaceutically acceptable carrier.

The invention thus further provides pharmaceutical formulations comprising a compound identified by methods of the invention or a pharmaceutically acceptable salt or derivative thereof together with one or more pharmaceutically acceptable carriers thereof and/or prophylactic ingredients. The carrier(s) are "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, can thus be placed into the form of pharmaceutical formulations and unit dosages thereof, and in such form can be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles, and such unit dosage forms can contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition can be made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient can also be administered by injection as a composition wherein, for example, saline, dextrose or water can be used as a suitable pharmaceutically acceptable carrier.

The invention provides a method for treating or preventing a metabolic-related disorder in an individual in need thereof, comprising administering to said individual an effective amount of the compound identified according to the method of: a) contacting a candidate compound with GPR43, and b) determining whether GPR43 functionality is modulated, wherein a modulation in GPR43 functionality is indicative of the candidate compound being a metabolic stabilizing compound. In some embodiments, said metabolic-related disorder is hypoglycemia, aging, insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In some embodiments, said metabolic-related disorder is Type II diabetes. In one embodiment, the compound administered comprises a GPR43 inverse agonist or antagonist. In one embodiment, the method further comprises administering to said individual an effective amount of an agent used for the treatment of diabetes, blood lipid disorders, or obesity in combination with an effective amount of the pharmaceutical composition comprising, consisting essentially of, or consisting of the metabolic stabilizing compound identified according to the method of: a) contacting a candidate compound with GPR43, and b) determining whether GPR43 functionality is modulated, wherein a modulation in GPR43 functionality is indicative of the candidate compound being a metabolic stabilizing compound. For example, in one embodiment, the method further comprises administering to said individual an effective amount of an agent used for the treatment of diabetes, blood lipid disorders, or obesity in combination with an effective amount of a pharmaceutical composition containing a GPR43 inverse agonist. In one embodiment, the individual is a mammal and in another embodiment the individual is a human. In one embodiment, said metabolic-related disorder is hypoglycemia and said compound administered comprises a GPR43 agonist.

As used herein the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. Similarly, the term "preventing" means prevention of the occurrence or onset of one or more symptoms associated with a particular disorder and does not necessarily mean the complete prevention of a disorder. The methods of the invention can be used to treat a metabolic-related disorder including, for example, diabetes.

The dose when using the compounds identified by methods of the invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds identified by methods of the invention. Representative doses of the present invention include, about 0.01 mg to about 1000 mg, about 0.01 to about 750 mg, about 0.01 to about 500 mg, 0.01 to about 250 mg, 0.01 mg to about 200 mg, about 0.01 mg to 150 mg, about 0.01 mg to about 100 mg, and about 0.01 mg to about 75 mg. Multiple doses can be administered during the day, especially when relatively large amounts are deemed to be needed, for example 2, 3 or 4, doses. If appropriate, depending on individual behavior and as appropriate from the patients physician or care-giver it can be necessary to deviate upward or downward from the daily dose.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. Typically, animal models include, but are not limited to, the rodent diabetes models (other animal models have been reported by Reed and Scribner in Diabetes, Obesity and Metabolism, 1:75-86 (1999)). In some circumstances, these extrapolations can merely be based on the weight of the animal model in comparison to another, such as a mammal, for example, a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds identified by methods of the invention and as part of a drug combination. The dosage regimen for treating a disease condition with the compounds and/or compositions of this invention is selected in accordance with a variety factors as cited above. Thus, the actual dosage regimen employed can vary widely and therefore can deviate from a preferred dosage regimen and one skilled in the art will recognize that dosage and dosage regimen outside these typical ranges can be tested and, where appropriate, can be used in the methods of this invention.

The desired dose can conveniently be presented in a single dose or as divided doses administered at appropriate intervals, for example, as two, three, four or more sub-doses per day. The sub-dose itself can be further divided, for example, into a number of discrete loosely spaced administrations. The daily dose can be divided, especially when relatively large amounts are administered as deemed appropriate, into several, for example 2, 3 or 4, part administrations. If appropriate, depending on individual behavior, it can be necessary to deviate upward or downward from the daily dose indicated.

The compounds identified by methods of the invention can be administrated in a wide variety of oral and parenteral dosage forms. It will be obvious to those skilled in the art that the following dosage forms can comprise, as the active component, either a compound disclosed herein or identified by methods of the invention or a pharmaceutically acceptable salt of a compound identified by methods of the invention.

For preparing pharmaceutical compositions from the compounds identified by methods of the invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which can also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted to the desire shape and size.

The powders and tablets can contain varying percentage amounts of the active compound. A representative amount in a powder or tablet can contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration can be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds according to the present invention can thus be formulated for parenteral administration (e.g. by injection, for example bolus injection or continuous infusion) and can be presented in unit dose form in ampoules, pre-filled syringes, small volume infusion or in multi-dose containers with an added preservative. The pharmaceutical compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

For topical administration to the epidermis the compounds according to the invention can be formulated as ointments, creams or lotions, or as a transdermal patch.

Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract can also be achieved by means of an aerosol formulation in which the active ingredient is provided in a pressurized pack with a suitable propellant. If the compounds identified by methods of the invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds identified by methods of the invention as an aerosol can be prepared by processes well-known to the person skilled in the art. For their preparation, for example, solutions or dispersions of the compounds identified by methods of the invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol can conveniently also contain a surfactant such as lecithin. The dose of drug can be controlled by provision of a metered valve.

In formulations intended for administration to the respiratory tract, including intranasal formulations, the compound will generally have a small particle size for example of the order of 10 microns or less. Such a particle size can be obtained by means known in the art; for example by micronization. When desired, formulations adapted to give sustained release of the active ingredient can be employed.

Alternatively the active ingredients can be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, for example, gelatin, or blister packs from which the powder can be administered by means of an inhaler.

The pharmaceutical preparations can be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are particularly useful compositions.

Metabolic-related disorders include, for example, hypoglycemia, aging, insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease.

Hypoglycemia is defined as abnormally low blood glucose. Hypoglycemia can result, for example, from excessive insulin or a poor diet. For example, hypoglycemia can occur when a person with diabetes has injected too much insulin, eaten too little food, or has exercized without extra food. Symptoms of hypoglycemia include, for example, a feeling of nervousness or weakness, headache, blurred vision, hunger, and excessive sweatiness.

Aging is the physiological processes that occur in an organism as it gets older. Caloric restriction down-regulates insulin secretion and there is reason to suspect that these effects are key mediators of caloric restriction's favorable impact on longevity. In addition, mutations in insulin, or the insulin signalling pathway, influence aging in *C. elegans*. Thus, strategies for down-regulating insulin can be useful to slow the process of aging and increase longevity.

Diabetes, obesity, and related conditions such as insulin resistance, impaired glucose tolerance and hyperglycemia have been described above herein. In some embodiments, said metabolic-related disorder includes hyperinsulinemia, hyperlipidemia, hypertriglyceridemia, hypercholesterolemia, dyslipidemia, atherosclerosis, heart disease, stroke, hypertension, Syndrome X and peripheral vascular disease.

Beta cells in the pancreas produce insulin. Insulin stimulates uptake of glucose from the blood to the cells in the body. As described above, when the body's cells are resistant to the action of the insulin, it is called insulin resistance. As a result of the insulin resistance, the pancreas produces much more insulin than normal. This is called hyperinsulinemia.

Dyslipidemia is a general term meaning a disregulation of lipid levels in the body. Hyperlipidemia is an elevation of lipids (fats) in the bloodstream. These lipids include cholesterol, cholesterol esters (compounds), phospholipids and triglycerides. They're transported in the blood as part of large molecules called lipoproteins. These are the five major families of blood (plasma) lipoproteins: chylomicrons, very low-density lipoproteins (VLDL), intermediate-density lipoproteins (IDL), low-density lipoproteins (LDL), high-density lipoproteins (HDL). When hyperlipidemia is defined in terms of a class or classes of elevated lipoproteins in the blood, the term hyperlipoproteinemia is used. Hypercholesterolemia is the term for high cholesterol levels in the blood. Hypertriglyceridemia refers to high triglyceride levels in the blood.

Atherosclerosis is a process where deposits of fatty substances, cholesterol and other substances build up in the inner lining of an artery. This buildup is called plaque. Plaques that rupture cause blood clots to form that can block blood flow to the heart (heart attack) or the brain (stroke). Heart attack is the number one cause of death for both and women in the United States and stroke is the number three cause of death [see, for example, Nature Medicine, Special Focus on Atherosclerosis, (2002) 8:1209-1262]. Abnormally high levels of circulating lipids are a major predisposing factor in development of atherosclerosis. Elevated levels of low density lipoprotein (LDL) cholesterol, elevated levels of triglycerides, or low levels of high density lipoprotein (HDL) cholesterol are, independently, risk factors for atherosclerosis and associated pathologies.

Heart disease includes, but is not limited to, cardiac insufficiency, coronary insufficiency, coronary artery disease, and high blood pressure (hypertension). Peripheral vascular disease refers to diseases of blood vessels outside the heart and brain. Organic peripheral vascular diseases are caused by structural changes in the blood vessels, such as inflammation and tissue damage. Peripheral artery disease is an example. Peripheral artery disease (PAD) is a condition similar to coronary artery disease and carotid artery disease. In PAD, fatty deposits build up along artery walls and affect blood circulation, mainly in arteries leading to the legs and feet. In its early stages a common symptom is cramping or fatigue in the legs and buttocks during activity. Such cramping subsides when the person stands still. This is called "intermittent claudication." People with PAD have a higher risk of death from stroke and heart attack, due to the risk of blood clots.

Syndrome X, also called metabolic syndrome, is characterized by a group of metabolic risk factors in one person. They include: central obesity (excessive fat tissue in and around the abdomen), atherogenic dyslipidemia (blood fat disorders—mainly high triglycerides and low HDL cholesterol), raised blood pressure (130/85 mmHg or higher), insulin resistance or glucose intolerance, prothrombotic state (e.g., high fibrinogen or plasminogen activator inhibitor [−1] in the blood), and proinflammatory state (e.g., elevated high-sensitivity C-reactive protein in the blood).

Hypertension is a common disorder in which blood pressure remains abnormally high (a reading of 140/90 mm Hg or greater). Several drugs are on the market which can treat hypertension. Hypertension is a risk factor for several serious conditions including stroke.

Peripheral vascular disease is the build-up of atherosclerotic plaque in the arteries outside of the heart. Symptoms of peripheral vascular disease depend on what artery is affected and how severely the blood flow is reduced. For example, one may experience a dull, cramping pain, numbness or tingling, or a change in skin color. Clinical studies have identified factors that increase the risk of peripheral vascular disease, such as diabetes or smoking. Peripheral vascular disease can be diagnosed using, for example, an ankle brachial index (ABI) test, an ultrasound Doppler test, or an angiogram. Peripheral vascular disease may be treated with medication, surgery, minimally invasive interventional procedures, or a combination of these therapies.

While the compounds identified by the methods of the invention can be administered as the sole active pharmaceutical agent as described herein above, they can also be used in combination with one or more agents including, for example, agents that are used for the treatment of diabetes, blood lipid disorders, or obesity. For example, a compound such as a GPR43 inverse agonist or antagonist can be used in combination with one or more agents belonging to the class of drugs known as α-glucosidase inhibitors, aldose reductase inhibitors, biguanides, thiazolidinediones, meglitinides, sulfonylureas, insulin, HMG-CoA reductase inhibitors, squalene synthesis inhibitors, fibrate compounds, LDL catabolism enhancers, angiotensin converting enzyme (ACE) inhibitors, lipase inhibitors, serotonin and/or noradrenaline releasers or reuptake inhibitors.

α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolamine (generic name; voglibose), miglitol, and α-glucosidase inhibitors known in the art.

The class of aldose reductase inhibitors are drugs which inhibit the first-stage rate-limiting enzyme in the polyol pathway and thereby prevent or arrest diabetic complications. In the hyperglycemic state of diabetes, the utilization of glucose in the polyol pathway is increased and the excess sorbitol accumulated intracellularly as a consequence acts as a tissue toxin and hence evokes the onset of complications such as diabetic neuropathy, retinopathy, and nephropathy. Examples of the aldose reductase inhibitors include tolurestat; epalrestat; 3,4-dihydro-2,8-diisopropyl-3-thioxo-2H-1,4-benzoxazine-4-acetic acid; 2,7-difluorospiro(9H-fluorene-9,4'-imidazolidine)-2',5'-dione (generic name: imirestat); 3-[(4-bromo-2-flurophenyl)methy]-7-chloro-3,4-dihydro-2,4-dioxo-1(2H)-quinazoline acetic acid (generic name: zenarestat); 6-fluoro-2,3-dihydro-2',5'-dioxo-spiro[4H-1-benzopyran-4,4'-imidazolidine]-2-carboxamide (SNK-860); zopolrestat; sorbinil; and 1-[(3-bromo-2-benzofuranyl)sulfonyl]-2,4-imidazolidinedione (M-16209), and aldose reductase inhibitors known in the art.

The biguanides are a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Insulin secretion enhancers belong to the class of drugs having the property to promote secretion of insulin from pancreatic β cells. Examples of the insulin secretion enhancers include sulfonylureas (SU). The sulfonylureas (SU) are drugs which promote secretion of insulin from pancreatic β cells by transmitting signals of insulin secretion via SU receptors in the cell membranes. Examples of the sulfonylureas include tolbutamide; chlorpropamide; tolazamide; acetohexamide; 4-chloro-N-[(1-pyrolidinylamino) carbonyl]-benzenesulfonamide (generic name: glycopyramide) or its ammonium salt; glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; tolcyclamide, glimepiride, and other insulin secretion enhancers known in the art. Other insulin secretion enhancers include N-[[4-(1-methylethyl)cyclohexyl)carbonyl]-D-phenylalanine (Nateglinide); calcium (2S)-2-benzyl-3-(cis-hexahydro-2-isoindolinylcarbonyl)propionate dihydrate (Mitiglinide, KAD-1229); and other insulin secretion enhancers known in the art.

Thiazolidinediones belong to the class of drugs more commonly known as TZDs. Thiazolidinediones are a class of drugs for type 2 diabetes that lower the blood sugar by increasing the sensitivity of cells to insulin. Insulin can then move glucose from the blood into cells for energy. These drugs can also increase HDL.

Examples of thiazolidinediones include rosiglitazone, pioglitazone, and thiazolidinediones known in the art. Rezulin (troglitazone) was the first drug in this class in the U.S., but was taken off the market because of liver toxicity. Sister compounds now available with a better safety profile include Actos (pioglitazone) and Avandia (rosiglitazone). The main contraindications to the use of these medications include liver disease and heart failure. These drugs can also cause a significant increase in fluid retention and thereby increase the risk of heart failure.

Meglitinides are used to stop the rapid rise in blood sugar that can occur immediately after a person with type 2 diabetes eats a meal. These compounds, which include, for example, repaglinide (Prandin) and nateglinide (Starlix), work by increasing the amount of insulin produced by the pancreas similar to the way sulfonyurea medications work. Meglitinides are taken before eating a meal. Side effects associated with this class of drugs includes low blood sugar, upper respiratory infections including sinus conditions, headache, joint and back pain, nausea, diarrhea and constipation.

The different types of insulin are categorized according to how fast they start to work (onset) and how long they continue to work (duration). The types now available include rapid-, short-, intermediate-, and long-acting insulin. There are premixed rapid- and intermediate-acting insulins available, including: 70% intermediate-acting (NPH) and 30% short-acting regular insulin, called 70/30 insulin; 50% intermediate-acting (NPH) and 50% short-acting regular insulin, called 50/50 insulin; 75% intermediate-acting (NPH) and 25% rapid-acting Humalog (lispro), called 75/25 insulin; 70% intermediate-acting (NPH); and 30% rapid-acting NovoLog (insulin aspart), called NovoLog Mix 70/30. Insulin usually is given as an injection into the tissues under the skin (subcutaneous). It can also be given through an insulin pump or jet injector, a device that sprays the medication into the skin.

Insulin lets sugar (glucose) enter cells, where it is used for energy. Without insulin, the blood sugar level rises above what is safe for the body. Usually, a rapid- or short-acting and an intermediate- or long-acting insulin is taken to provide the constant and variable levels of insulin that the body needs. The short-acting insulin reduces blood sugar levels quickly and then wears off. Some long-acting insulins start taking effect when rapid- or short-acting insulins begin to wear off. The new long-acting insulin, Lantus, starts to work within a few minutes after it is given and continues to work at the same rate for about 24 hours.

The combination of a rapid- or short-acting and intermediate- or long-acting insulin helps keep blood sugar levels within a range that is safe for the body throughout the day. Thus insulin can be used to treat people with type 1 diabetes, people with type 2 diabetes whose pancreas produces little or no insulin or whose oral medications do not control their blood sugar. These people may take insulin either alone or along with oral medication, people with type 2 diabetes whose blood sugar levels are high because of a severe illness or major surgery, women with type 2 diabetes who are pregnant or breast-feeding who cannot keep their blood sugar levels within a safe range with diet and exercise. Only one oral diabetes medication (glyburide) has been studied for use during pregnancy.

The major side effect of insulin can be a dangerously low blood sugar level (severe hypoglycemia). A very low blood sugar level can develop within 10 to 15 minutes. Insulin can contribute to weight gain, especially in people with type 2 who already are overweight. Other possible side effects of long-term insulin use include the loss of fatty tissue (lipodystrophy) where the insulin is injected and, rarely, allergic reactions that include swelling (edema).

Statin compounds belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. A statin that inhibits this reductase lowers serum LDL concentrations by upregulating the activity of LDL receptors and responsible for clearing LDL from the blood. Examples of the statin compounds include rosuvastatin, pravastatin and its sodium salt, simvastatin, lovastatin, atorvastatin, fluvastatin, cerivastatin, and HMG-CoA reductase inhibitors known in the art.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

LDL (low-density lipoprotein) catabolism enhancers belong to a class of drugs that lower blood cholesterol levels by increasing the number of LDL (low-density lipoprotein) receptors, examples include LDL catabolism enhancers known in the art.

Angiotensin converting enzyme (ACE) inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Lipase inhibitors include, for example, anti-obesity compounds such as Orlistat (XENICAL™). Orlistat inhibits fat absorption directly but also tends to produce a high incidence of unpleasant gastric side-effects such as diarrhea and flatulence.

Another class of anti-obesity drugs includes serotonin and/or noradrenaline releasers or reuptake inhibitors. For example, sibutramine (Meridia™) is a mixed 5-HT/noradrenaline reuptake inhibitor. The main side effect of sibutramine can be an increase in blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn from use after reports of preliminary evidence of heart valve abnormalities associated with their use.

Some embodiments of the invention include, a pharmaceutical composition comprising a compound disclosed herein or identified by methods of the invention or a pharmaceutically acceptable salt thereof in combination with at least one member selected from the group consisting of an α-glucosidase inhibitor, an aldose reductase inhibitor, a biguanide, a HMG-CoA reductase inhibitor, a squalene synthesis inhibitor, a fibrate compound, a LDL catabolism enhancer and an angiotensin converting enzyme inhibitor. In another embodiment, the HMG-CoA reductase inhibitor is selected from the group consisting of prevastatin, simvastatin, lovastatin, atorvastatin, fluvastatin and lipitor.

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds are administered as a combination therapy or prophylaxis with another active compound the therapeutic agents can be formulated as a separate pharmaceutical compositions given at the same time or at different times, or the therapeutic agents can be given as a single composition.

The invention also provides a method for the manufacture of a medicament comprising a pharmaceutical composition comprising, consisting essentially of, or consisting of the metabolic stabilizing compound identified according to the method of: a) contacting a candidate compound with GPR43, and b) determining whether GPR43 functionality is modulated, wherein a modulation in GPR43 functionality is indicative of the candidate compound being a metabolic stabilizing compound, for use as a metabolic stabilizing compound.

The invention further provides a method for the manufacture of a medicament comprising a pharmaceutical composition comprising, consisting essentially of, or consisting of the metabolic stabilizing compound identified according to the method of: a) contacting a candidate compound with GPR43, and b) determining whether GPR43 functionality is modulated, wherein a modulation in GPR43 functionality is indicative of the candidate compound being a metabolic stabilizing compound, for use in the treatment of a metabolic-related disease.

The invention relates to a method for identifying a metabolic stabilizing compound, comprising: a) contacting a candidate compound with GPR43, and b) determining whether GPR43 functionality is increased, wherein an increase in GPR43 functionality is indicative of the candidate compound being a metabolic stabilizing compound.

In one embodiment, said GPR43 is derived from a mammal. In another embodiment, said GPR43 is human.

In certain embodiments, said GPR43 is recombinant. In certain embodiments, said contacting comprises contacting with a host cell or with membrane of a host cell that expresses the GPCR, wherein the host cell comprises an expression vector comprising a polynucleotide encoding the receptor. In some embodiments, said contacting is carried out in the presence of a known agonist of the GPCR or an agonist as disclosed herein.

In certain embodiments, said method further comprises the step of comparing the increase in functionality of the receptor caused by the candidate compound to a second increase in functionality of the receptor caused by contacting the receptor with a known ligand or agonist of the receptor.

In some embodiments, said determining comprises a second messenger assay, for example, determining is through the measurement of GTPγS binding to membrane comprising said GPCR. In certain embodiments, said GTPγS is labeled with [$^{35}$S]. In certain embodiments, said determining is through the measurement of the level of a second messenger selected from the group consisting of cyclic AMP (cAMP), cyclic GMP (cGMP), inositol triphosphate (IP3), diacylglycerol (DAG), MAP kinase activity, and $Ca^{2+}$. In certain embodiments, said second messenger is cAMP. In certain embodiments, said measurement of cAMP is carried out using whole-cell adenylyl cyclase assay. In certain embodiments, said measurement of cAMP is carried out with membrane comprising said GPCR. In certain embodiments, said determining is through measurement of intracellular IP3. In certain embodiments, said second messenger is MAP kinase activity. In some embodiments, said determining is through CRE-reporter assay. In certain embodiments, said reporter is luciferase. In some embodiments, said reporter is β-galactosidase. In certain embodiments, said determining or said comparing is through measurement of intracellular $Ca^{2+}$.

In some embodiments, said determining is through measurement of glucose uptake by adipocytes obtained from a mammal.

In certain embodiments, said determining is through the use of a melanophore assay.

In certain embodiments, said GPR43 is recombinant. In certain embodiments, said contacting comprises contacting with a host cell or with membrane of a host cell that expresses the GPCR, wherein the host cell comprises an expression vector comprising a polynucleotide encoding the receptor. In some embodiments, said contacting is carried out in the presence of an agonist of the GPCR.

In the methods of the invention, control reactions can be performed to show specificity of the response. For example, mock-transfected cells can be compared to GPR43 transfected cells to show specificity of a response to the GPR43 receptor.

In the methods of the invention, in certain embodiments, said candidate compound is not an antibody or antigen-binding derivative thereof. In certain embodiments, said candidate compound is not a peptide. In certain embodiments, said candidate compound is not a polypeptide.

In the methods of the invention, determining can comprise a second messenger assay. The initiation of an intracellular signal can be determined, for example, through the measurement of the level of a second messenger such as cyclic AMP (cAMP), cyclic GMP (cGMP), inositol triphosphate (IP3), diacylglycerol (DAG), MAP kinase, or calcium. Several assays are well known in the art for measuring these second messengers, for example, cAMP assays, IP3 assays, the FLIPR assay, the melanophore assay, or CRE-reporter assay. In addition, examples of second messenger assays are disclosed herein in Examples 6-11. In certain embodiments, said second messenger is cAMP. In other embodiments, said second messenger is IP3. In further embodiments said second messenger is calcium.

In one embodiment, said determining is through the measurement of GTPγS binding to membrane comprising said GPCR. Such assays are well known in the art and exemplified herein in Examples 6 and 8. In certain embodiments, said GTPγS is labeled with [$^{35}$S].

The invention also relates to a metabolic stabilizing compound identifiable according to the method of: a) contacting a candidate compound with GPR43, and b) determining whether GPR43 functionality is increased, wherein an increase in GPR43 functionality is indicative of the candidate compound being a metabolic stabilizing compound.

For example, the invention relates to a metabolic stabilizing compound identified according to the method of: a) contacting a candidate compound with GPR43, and b) determining whether GPR43 functionality is increased, wherein an increase in GPR43 functionality is indicative of the candidate compound being a metabolic stabilizing compound.

In one embodiment, said metabolic stabilizing compound is a GPR43 agonist. In some embodiments, said agonist is material not previously known to activate an intracellular response when it binds to the GPR43 receptor.

In some embodiments, said metabolic stabilizing compound is a GPR43 agonist with an EC50 of less than 10 μM, of less than 1 μM, of less than 100 nM, or of less than 10 nM. In some embodiments, said metabolic stabilizing compound is an agonist with an EC50 of a value selected from the interval of 1 nM to 10 μM. In some embodiments, said metabolic stabilizing compound is an agonist with an EC50 of a value selected from the interval of 1 nM to 1 μM. In some embodiments, said metabolic stabilizing compound is an agonist with an EC50 of a value selected from the interval of 1 nM to 100 nM. In some embodiments, said metabolic stabilizing compound is an agonist with an EC50 of a value selected from the interval of 1 nM to 10 nM.

In certain embodiments, said EC50 is determined using an assay selected from the group consisting of: IP3 assay carried out using transfected HEK293 cells expressing recombinant GPR43 polypeptide; and melanophore assay carried out using transfected melanophores expressing recombinant GPR43 polypeptide. In some embodiments, said metabolic stabilizing compound is an agonist with an EC50 of less than 10 μM, of less than 1 μM, of less than 100 nM, or of less than 10 nM in said assay. In some embodiments, said metabolic stabilizing compound is an agonist with an EC50 of less than 10 μM in said assay. In some embodiments, said metabolic stabilizing compound is an agonist with an EC50 of less than 9 μM in said assay. In some embodiments, said metabolic stabilizing compound is an inverse agonist or antagonist with an EC50 of less than 8 μM in said assay. In some embodiments, said metabolic stabilizing compound is an agonist with an EC50 of less than 7 μM in said assay. In some embodiments, said metabolic stabilizing compound is an agonist with an EC50 of less than 6 μM in said assay. In some embodiments, said metabolic stabilizing compound is an agonist with an EC50 of less than 5 μM in said assay. In some embodiments, said metabolic stabilizing compound is an agonist with an EC50 of less than 4 μM in said assay. In some embodiments, said metabolic stabilizing compound is an agonist with an EC50 of less than 3 μM in said assay. In some embodiments, said metabolic stabilizing compound is an agonist with an EC50 of less than 2 μM in said assay. In some embodiments, said metabolic stabilizing compound is an agonist with an EC50 of less than 1 μM in said assay. In some embodiments, said metabolic stabilizing compound is an agonist with an EC50 of less than 900 nM in said assay. In some embodiments, said metabolic stabilizing compound is an agonist with an EC50 of less than 800 nM in said assay. In some embodiments, said metabolic stabilizing compound is an agonist with an EC50 of less than 700 nM in said assay. In some embodiments, said metabolic stabilizing compound is an agonist with an EC50 of less than 600 nM in said assay. In some embodiments, said metabolic stabilizing compound is an agonist with an EC50 of less than 500 nM in said assay. In some embodiments, said metabolic stabilizing compound is an agonist with an EC50 of less than 400 nM n said assay. In some embodiments, said metabolic stabilizing compound is an agonist with an EC50 of less than 300 nM in said assay. In some embodiments, said metabolic stabilizing compound is an agonist with an EC50 of less than 200 nM in said assay. In some embodiments, said metabolic stabilizing compound is an agonist with an EC50 of less than 100 nM in said assay. In some embodiments, said metabolic stabilizing compound is an agonist with an EC50 of less than 90 nM in said assay. In some embodiments, said metabolic stabilizing compound is an agonist with an EC50 of less than 80 nM in said assay. In some embodiments, said metabolic stabilizing compound is an agonist with an EC50 of less than 70 nM in said assay. In some embodiments, said metabolic stabilizing compound is an agonist with an EC50 of less than 60 nM in said assay. In some embodiments, said metabolic stabilizing compound is an agonist with an EC50 of less than 50 nM in said assay. In some embodiments, said metabolic stabilizing compound is an agonist with an EC50 of less than 40 nM n said assay. In some embodiments, said metabolic stabilizing compound is an agonist with an EC50 of less than 30 nM in said assay. In some embodiments, said metabolic stabilizing compound is an agonist with an EC50 of less than 20 nM in said assay. In some embodiments, said metabolic stabilizing compound is an agonist with an EC50 of less than 10 nM in said assay. In some embodiments, said metabolic stabilizing compound is an agonist with an EC50 in said assay of a value selected from the interval of 1 nM to 10 µM. In some embodiments, said metabolic stabilizing compound is an agonist with an EC50 in said assay of a value selected from the interval of 1 nM to 1 µM. In some embodiments, said metabolic stabilizing compound is an agonist with an EC50 in said assay of a value selected from the interval of 1 nM to 100 nM. In some embodiments, said metabolic stabilizing compound is an agonist with an EC50 in said assay of a value selected from the interval of 1 nM to 10 nM. In some embodiments, said metabolic stabilizing compound is selective for the GPCR.

In some embodiments, said metabolic stabilizing compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said orally bioavailable metabolic stabilizing compound is further able to cross the blood-brain barrier.

In addition, the invention relates to a method for preparing a composition which comprises identifying a metabolic stabilizing compound and then admixing said compound with a carrier, wherein said compound is identifiable by the method of: a) contacting a candidate compound with GPR43, and b) determining whether GPR43 functionality is increased, wherein an increase in GPR43 functionality is indicative of the candidate compound being a metabolic stabilizing compound. For example, the invention relates to a method for preparing a composition which comprises identifying a metabolic stabilizing compound and then admixing said compound with a carrier, wherein said compound is identified by the method of: a) contacting a candidate compound with GPR43, and b) determining whether GPR43 functionality is increased, wherein an increase in GPR43 functionality is indicative of the candidate compound being a metabolic stabilizing compound.

The invention also relates to a pharmaceutical composition comprising, consisting essentially of, or consisting of the metabolic stabilizing compound identified according to the method of: a) contacting a candidate compound with GPR43, and b) determining whether GPR43 functionality is increased, wherein an increase in GPR43 functionality is indicative of the candidate compound being a metabolic stabilizing compound.

Some embodiments of the present invention include a method of producing a pharmaceutical composition comprising admixing at least one compound according to any of the compound embodiments disclosed herein and a pharmaceutically acceptable carrier.

A compound can be formulated into pharmaceutical compositions using techniques well known to those in the art and described herein.

While it is possible that, for use in the prophylaxis or treatment, a compound disclosed herein or identified by methods of the invention can in an alternative use be administered as a raw or pure chemical, it can be useful to present the compound or active ingredient as a pharmaceutical formulation or composition further comprising a pharmaceutically acceptable carrier.

The invention thus further provides pharmaceutical formulations comprising a compound disclosed herein or identified by methods of the invention or a pharmaceutically acceptable salt or derivative thereof together with one or more pharmaceutically acceptable carriers thereof and/or prophylactic ingredients. The carrier(s) are "acceptable" in the sense of being compatible with the other ingredients of the formulation and not overly deleterious to the recipient thereof.

Pharmaceutical formulations, routes of administration, and dosages have been described above.

The invention relates to a method for treating or preventing a metabolic-related disorder in an individual in need thereof, comprising administering to said individual an effective amount of the compound identified according to the method of: a) contacting a candidate compound with GPR43, and b) determining whether GPR43 functionality is increased, wherein an increase in GPR43 functionality is indicative of the candidate compound being a metabolic stabilizing compound. In some embodiments, said metabolic-related disorder is hypoglycemia or aging. In one embodiment, the compound administered comprises a GRP43 agonist. In one embodiment, the individual is a mammal and in another embodiment the individual is a human.

While the compounds identified by the methods of the invention can be administered as the sole active pharmaceutical agent as described herein above, they can also be used in combination with one or more agents.

The invention also relates to a method for the manufacture of a medicament comprising a pharmaceutical composition comprising, consisting essentially of, or consisting of the metabolic stabilizing compound identified according to the method of: a) contacting a candidate compound with GPR43, and b) determining whether GPR43 functionality is increased, wherein an increase in GPR43 functionality is indicative of the candidate compound being a metabolic stabilizing compound, for use as a metabolic stabilizing compound.

The invention further relates to a method for the manufacture of a medicament comprising a pharmaceutical composition comprising, consisting essentially of, or consisting of the metabolic stabilizing compound identified according to the method of: a) contacting a candidate compound with GPR43, and b) determining whether GPR43 functionality is increased, wherein an increase in GPR43 functionality is indicative of the candidate compound being a metabolic stabilizing compound, for use in the treatment of a metabolic-related disease.

The invention provides a method for identifying a metabolic stabilizing compound, comprising: a) contacting a candidate compound with GPR43, and b) determining whether GPR43 functionality is decreased, wherein a decrease in GPR43 functionality is indicative of the candidate compound being a metabolic stabilizing compound.

In some embodiments, said metabolic stabilizing compound is a blood glucose stabilizing compound. In some embodiments, said metabolic stabilizing compound is an insulin secretion modulator.

In one embodiment, said GPR43 is derived from a mammal. In another embodiment, said GPR43 is human.

In certain embodiments, said GPR43 is recombinant. In certain embodiments, said contacting comprises contacting with a host cell or with membrane of a host cell that expresses the GPCR, wherein the host cell comprises an expression vector comprising a polynucleotide encoding the receptor. In some embodiments, said contacting is carried out in the presence of a known agonist of the GPCR.

In some embodiments, said determining comprises a second messenger assay, for example, determining is through the measurement of GTPγS binding to membrane comprising said GPCR. In certain embodiments, said GTPγS is labeled with [$^{35}$S]. In certain embodiments, said determining is through the measurement of the level of a second messenger selected from the group consisting of cyclic AMP (cAMP), cyclic GMP (cGMP), inositol triphosphate (IP3), diacylglycerol (DAG), MAP kinase activity, and $Ca^{2+}$. In certain embodiments, said second messenger is cAMP. In certain embodiments, said measurement of cAMP is carried out using whole-cell adenylyl cyclase assay. In certain embodiments, said measurement of cAMP is carried out with membrane comprising said GPCR. In certain embodiments, said determining is through measurement of intracellular IP3. In certain embodiments, said second messenger is MAP kinase activity. In some embodiments, said determining is through CRE-reporter assay. In certain embodiments, said reporter is luciferase. In some embodiments, said reporter is β-galactosidase. In certain embodiments, said determining or said comparing is through measurement of intracellular $Ca^{2+}$, for example, using a FLIPR assay.

In some embodiments, said determining is through measurement of glucose uptake by adipocytes obtained from a mammal.

In certain embodiments, said determining is through the use of a melanophore assay.

In the methods of the invention, control reactions can be performed to show specificity of the response. For example, mock-transfected cells can be compared to GPR43 transfected cells to show specificity of a response to the GPR43 receptor.

In the methods of the invention, in certain embodiments, said candidate compound is not an antibody or antigen-binding derivative thereof. In certain embodiments, said candidate compound is not a peptide. In certain embodiments, said candidate compound is not a polypeptide.

In the methods of the invention, determining can comprise a second messenger assay. The initiation of an intracellular signal can be determined, for example, through the measurement of the level of a second messenger such as cyclic AMP (cAMP), cyclic GMP (cGMP), inositol triphosphate (IP3), diacylglycerol (DAG), MAP kinase, or calcium. Several assays are well known in the art for measuring these second messengers, for example, cAMP assays, IP3 assays, the FLIPR assay, the melanophore assay, or CRE-reporter assay. In addition, examples of second messenger assays are disclosed herein in Examples 6-11. In certain embodiments, said second messenger is cAMP. In other embodiments, said second messenger is IP3. In further embodiments said second messenger is calcium.

In one embodiment, said determining is through the measurement of GTPγS binding to membrane comprising said GPCR. Such assays are well known in the art and exemplified herein in Examples 6 and 8. In certain embodiments, said GTPγS is labeled with [$^{35}$S].

The invention also relates to a metabolic stabilizing compound identifiable according to the method of: a) contacting a candidate compound with GPR43, and b) determining whether GPR43 functionality is decreased, wherein a decrease in GPR43 functionality is indicative of the candidate compound being a metabolic stabilizing compound.

For example, the invention provides a metabolic stabilizing compound identified according to the method of: a) contacting a candidate compound with GPR43, and b) determining whether GPR43 functionality is decreased, wherein a decrease in GPR43 functionality is indicative of the candidate compound being a metabolic stabilizing compound.

In one embodiment, said metabolic stabilizing compound is a GPR43 inverse agonist. In one embodiment, said metabolic stabilizing compound is a GPR43 antagonist.

In some embodiments, said metabolic stabilizing compound is a GPR43 inverse agonist or antagonist with an IC50 of less than 10 μM, of less than 1 μM, of less than 100 nM, or of less than 10 nM. In some embodiments, said metabolic stabilizing compound is an inverse agonist or antagonist with an IC50 of a value selected from the interval of 1 nM to 10 μM. In some embodiments, said metabolic stabilizing compound is an inverse agonist or antagonist with an IC50 of a value selected from the interval of 1 nM to 1 μM. In some embodiments, said metabolic stabilizing compound is an inverse agonist or antagonist with an IC50 of a value selected from the interval of 1 nM to 100 nM. In some embodiments, said metabolic stabilizing compound is an inverse agonist or antagonist with an IC50 of a value selected from the interval of 1 nM to 10 nM.

In certain embodiments, said IC50 is determined using an assay selected from the group consisting of: IP3 assay carried out using transfected HEK293 cells expressing recombinant GPR43 polypeptide; and melanophore assay carried out using transfected melanophores expressing recombinant GPR 43 polypeptide. In some embodiments, said metabolic stabilizing compound is an inverse agonist or antagonist with an IC50 of less than 10 μM, of less than 1 μM, of less than 100 nM, or of less than 10 nM in said assay. In some embodiments, said metabolic stabilizing compound is an inverse agonist or antagonist with an IC50 of less than 10 μM in said assay. In some embodiments, said metabolic stabilizing compound is an inverse agonist or antagonist with an IC50 of less than 9 μM in said assay. In some embodiments, said metabolic stabilizing compound is an inverse inverse agonist or antagonist or antinverse agonist or antagonist with an IC50 of less than 8 μM in said assay. In some embodiments, said metabolic stabilizing compound is an inverse agonist or antagonist with an IC50 of less than 7 μM in said assay. In some embodiments, said metabolic stabilizing compound is an inverse agonist or antagonist with an IC50 of less than 6 μM in said assay. In some embodiments, said metabolic stabilizing compound is an inverse agonist or antagonist with an IC50 of less than 5 μM in said assay. In some embodiments, said metabolic stabilizing compound is an inverse agonist or antagonist with an IC50 of less than 4 μM in said assay. In some embodiments, said metabolic stabilizing compound is an inverse agonist or antagonist with an IC50 of less than 3 μM in said assay. In some embodiments, said metabolic stabilizing compound is an inverse agonist or antagonist with an IC50 of less than 2 μM in said assay. In some embodiments, said metabolic stabilizing compound is an inverse agonist or antagonist with an IC50 of less than 1 μM in said assay. In some embodiments, said metabolic stabilizing compound is an inverse agonist or antagonist with an IC50 of less than 900 nM in said assay. In some embodiments, said metabolic stabilizing compound is an inverse agonist or antagonist with an IC50 of less than 800 nM in said assay. In some embodiments, said metabolic stabilizing compound is an inverse agonist or antagonist with an IC50 of less than 700 nM in said assay. In some embodiments, said metabolic stabilizing compound is an inverse agonist or antagonist with an IC50 of less than 600 nM in said assay. In some embodiments, said metabolic stabilizing compound is an inverse agonist or antagonist with an IC50 of less than 500 nM in said assay. In some embodiments, said metabolic stabilizing compound is an inverse agonist or antagonist with an IC50 of less than 400 nM n said assay. In some embodiments, said metabolic stabilizing compound is an inverse agonist or antagonist with an IC50 of less than 300 nM in said assay. In some embodiments, said metabolic stabilizing compound is an inverse agonist or antagonist with an IC50 of less than 200 nM in said assay. In some embodiments, said metabolic stabilizing compound is an inverse agonist or antagonist with an IC50 of less than 100 nM in said assay. In some embodiments, said metabolic stabilizing compound is an inverse agonist or antagonist with an IC50 of less than 90 nM in said assay. In some embodiments, said metabolic stabilizing compound is an inverse agonist or antagonist with an IC50 of less than 80 nM in said assay. In some embodiment; said metabolic stabilizing compound is an inverse agonist or antagonist with an IC50 of less than 70 nM in said assay. In some embodiments, said metabolic stabilizing compound is an inverse agonist or antagonist with an IC50 of less than 60 nM in said assay. In some embodiments, said metabolic stabilizing compound is an inverse agonist or antagonist with an IC50 of less than 50 nM in said assay. In some, embodiments, said metabolic stabilizing compound is an inverse agonist or antagonist with an IC50 of less than 40 nM n said assay. In some embodiments, said metabolic stabilizing compound is an inverse agonist or antagonist with an IC50 of less than 30 nM in said assay. In some embodiments, said metabolic stabilizing compound is an inverse agonist or antagonist with an IC50 of less than 20 nM in said assay. In some embodiments, said metabolic stabilizing compound is an inverse agonist or antagonist with an IC50 of less than 10 nM in said assay. In some embodiments, said metabolic stabilizing compound is an inverse agonist or antagonist with an IC50 in said assay of a value selected from the interval of 1 nM to 10 µM. In some embodiments, said metabolic stabilizing compound is an inverse agonist or antagonist with an IC50 in said assay of a value selected from the interval of 1 nM to 1 µM. In some embodiments, said metabolic stabilizing compound is an inverse agonist or antagonist with an IC50 in said assay of a value selected from the interval of 1 nM to 100 nM. In some embodiments, said metabolic stabilizing compound is an inverse agonist or antagonist with an IC50 in said assay of a value selected from the interval of 1 nM to 10 nM. In some embodiments, said metabolic stabilizing compound is selective for the GPCR.

In some embodiments, said metabolic stabilizing compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said orally bioavailable metabolic stabilizing compound is further able to cross the blood-brain barrier.

In addition, the invention relates to a method for preparing a composition which comprises identifying a metabolic stabilizing compound and then admixing said compound with a carrier, wherein said compound is identifiable by the method of: a) contacting a candidate compound with GPR43, and b) determining whether GPR43 functionality is decreased, wherein a decrease in GPR43 functionality is indicative of the candidate compound being a metabolic stabilizing compound. For example, the invention provides a method for preparing a composition which comprises identifying a metabolic stabilizing compound and then admixing said compound with a carrier, wherein said compound is identified by the method of a) contacting a candidate compound with GPR43, and b) determining whether GPR43 functionality is decreased, wherein a decrease in GPR43 functionality is indicative of the candidate compound being a metabolic stabilizing compound.

The invention also provides a pharmaceutical composition comprising, consisting essentially of, or consisting of the metabolic stabilizing compound identified according to the method of: a) contacting a candidate compound with GPR43, and b) determining whether GPR43 functionality is decreased, wherein a decrease in GPR43 functionality is indicative of the candidate compound being a metabolic stabilizing compound.

Some embodiments of the present invention include a method of producing a pharmaceutical composition comprising admixing at least one compound according to any of the compound embodiments disclosed herein and a pharmaceutically acceptable carrier.

Pharmaceutical formulations, routes of administration, and dosages have been described above.

The invention provides a method for treating or preventing a metabolic-related disorder in an individual in need thereof, comprising administering to said individual an effective amount of the compound identified according to the method of a) contacting a candidate compound with GPR43, and b) determining whether GPR43 functionality is decreased, wherein a decrease in GPR43 functionality is indicative of the candidate compound being a metabolic stabilizing compound. In some embodiments, said metabolic-related disorder is insulin resistance, impaired glucose tolerance, or diabetes. In some embodiments, said metabolic-related disorder includes hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In one embodiment, said metabolic-related disorder is Type II diabetes. In one embodiment, the compound administered comprises a GRP43 inverse agonist or antagonist.

In one embodiment, the method further comprises administering to said individual an effective amount of an agent used for the treatment of diabetes, blood lipid disorders, or obesity in combination with an effective amount of the pharmaceutical composition comprising, consisting essentially of, or consisting of the metabolic stabilizing compound identified according to the method of: a) contacting a candidate compound with GPR43, and b) determining whether GPR43 functionality is decreased, wherein a decrease in GPR43 functionality is indicative of the candidate compound being a metabolic stabilizing compound. For example, in one embodiment, the method further comprises administering to said individual an effective amount of an agent used for the treatment of diabetes, blood lipid disorders, or obesity in combination with an effective amount of a pharmaceutical composition containing a GPR43 inverse agonist.

In one embodiment, the individual is a mammal and in another embodiment the individual is a human.

While the compounds identified by the methods of the invention can be administered as the sole active pharmaceutical agent as described herein above, they can also be used in combination with one or more agents including, for example, agents that are used for the treatment of diabetes, blood lipid disorders, or obesity. For example, a compound such as a GPR43 inverse agonist or antagonist can be used in combination with one or more agents belonging to the class of drugs known as α-glucosidase inhibitors, aldose reductase inhibitors, biguanides, thiazolidinediones, meglitinides, sulfonylureas, insulin, HMG-CoA reductase inhibitors, squalene synthesis inhibitors, fibrate compounds, LDL catabolism enhancers, angiotensin converting enzyme (ACE) inhibitors, lipase inhibitors, serotonin and/or noradrenaline releasers or reuptake inhibitors.

Some embodiments of the invention include, a pharmaceutical composition comprising a compound identified by methods of the invention or a pharmaceutically acceptable salt thereof in combination with at least one member selected from the group consisting of an α-glucosidase inhibitor, an aldose reductase inhibitor, a biguanide, a HMG-CoA reductase inhibitor, a squalene synthesis inhibitor, a fibrate compound, a LDL catabolism enhancer and an angiotensin converting enzyme inhibitor. In another embodiment, the HMG-CoA reductase inhibitor is selected from the group consisting of prevastatin, simvastatin, lovastatin, atorvastatin, fluvastatin and lipitor.

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds are administered as a combination therapy or prophylaxis with another active compound the therapeutic agents can be formulated as a separate pharmaceutical compositions given at the same time or at different times, or the therapeutic agents can be given as a single composition.

The invention also provides a method for the manufacture of a medicament comprising a pharmaceutical composition comprising, consisting essentially of, or consisting of the metabolic stabilizing compound identified according to the method of a) contacting a candidate compound with GPR43, and b) determining whether GPR43 functionality is decreased, wherein a decrease in GPR43 functionality is indicative of the candidate compound being a metabolic stabilizing compound, for use as a metabolic stabilizing compound.

The invention further provides a method for the manufacture of a medicament comprising a pharmaceutical composition comprising, consisting essentially of, or consisting of the metabolic stabilizing compound identified according to the method of: a) contacting a candidate compound with GPR43, and b) determining whether GPR43 functionality is decreased, wherein a decrease in GPR43 functionality is indicative of the candidate compound being a metabolic stabilizing compound, for use in the treatment of a metabolic-related disease.

The invention also relates to a method for increasing GPR43 function, comprising contacting GPR43 with an effective amount of a GPR43 agonist. The invention also relates to a method for increasing GPR43 function in a cell, comprising contacting a cell expressing GPR43 with an effective amount of a GPR43 agonist. The cell can be, for example, in an individual or the cell can be an isolated cell. In some embodiments, said agonist is material not previously known to activate an intracellular response when it binds to the GPR43 receptor.

The invention also relates to a method for decreasing GPR43 function, comprising contacting GPR43 with an effective amount of a GPR43 inverse agonist or antagonist. The invention also relates to a method for decreasing GPR43 function in a cell, comprising contacting a cell expressing GPR43 with an effective amount of a GPR43 inverse agonist or antagonist. The cell can be, for example, in an individual or the cell can be an isolated cell.

The invention provides a method for treating or preventing a metabolic-related disorder, comprising administering to an individual in need thereof an effective amount of a GPR43 modulator.

In one embodiment, said metabolic-related disorder is hypoglycemia or aging. In one embodiment, said modulator is an agonist. In some embodiments, said agonist is material not previously known to activate an intracellular response when it binds to the GPR43 receptor.

In one embodiment, said metabolic-related disorder is insulin resistance, impaired glucose tolerance, or diabetes. In some embodiments, said metabolic-related disorder includes hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In one embodiment said modulator is an inverse agonist or antagonist. In one embodiment said method further comprising administering to said individual an effective amount of an agent used for the treatment of diabetes, blood lipid disorders, or obesity in combination with an effective amount of a GPR43 inverse agonist or antagonist. In one embodiment, said metabolic-related disorder is insulin resistance, impaired glucose tolerance or diabetes. In one embodiment, said metabolic-related disorder is Type II diabetes. In one embodiment, the individual is a mammal and in another embodiment the individual is a human.

The invention relates to a method for treating or preventing a disorder treatable or preventable by increasing GPR43 function, comprising administering to an individual in need thereof an effective amount of a GPR43 agonist. In one embodiment, said disorder is a metabolic-related disorder. In some embodiments, said metabolic-related disorder is hypoglycemia or aging. In some embodiments, said agonist is material not previously known to activate an intracellular response when it binds to the GPR43 receptor.

The invention provides a method for treating or preventing a disorder treatable or preventable by decreasing GPR43 function, comprising administering to an individual in need thereof an effective amount of a GPR43 inverse agonist or antagonist. In one embodiment, said disorder is a metabolic-related disorder. In one embodiment said metabolic-related disorder is insulin resistance, impaired glucose tolerance, diabetes, hyperglycemia, hyperinsulinemia, hyperlipidemia, hypertriglyceridemia, hypercholesterolemia, dyslipidemia, obesity, Syndrome X, atherosclerosis, heart disease, stroke, hypertension, or peripheral vascular disease. In some embodiments, said metabolic-related disorder is insulin resistance, impaired glucose tolerance, or diabetes. In one embodiment, said metabolic-related disorder is type II diabetes. In one embodiment, said method further comprises administering to said individual an effective amount of an agent used for the treatment of diabetes, blood lipid disorders, or obesity in combination with an effective amount of a GPR43 inverse agonist or antagonist. In one embodiment, the individual is a mammal and in another embodiment the individual is a human.

The invention also relates to a method for increasing blood glucose levels in an individual in need thereof, comprising administering to the individual an effective amount of a GPR43 agonist. The invention also relates to a method for decreasing blood glucose levels in an individual in need thereof, comprising administering to the individual an effective amount of a GPR43 inverse agonist or antagonist.

In addition, the invention relates to a method for decreasing insulin secretion in an individual in need thereof, comprising administering to the individual an effective amount of a GPR43 agonist.

One object of the invention relates to a method of a) performing a method of the invention to identify a metabolic stabilizing compound and (b) optionally, determining the structure of the compound, and (c) providing the compound or the name or structure of the compound. In addition, the invention relates to a method of a) performing a method of the invention to identify a metabolic stabilizing compound and (b) optionally, determining the structure of the compound, (c) optionally, providing the name or structure of the compound, and (d) producing or synthesizing the compound. The invention further relates to a process for modulating the functionality of a GPCR comprising performing a method of the invention to identify a metabolic stabilizing compound and then contacting the GPCR with the metabolic stabilizing compound or administering the metabolic stabilizing compound to an individual under conditions sufficient to modulate the functionality of the GPCR.

Applicants reserve the right to exclude any one or more candidate compounds from any of the embodiments of the invention. Applicants also reserve the right to exclude any one or more modulators from any of the embodiments of the invention. Applicants further reserve the right to exclude any polynucleotide or polypeptide from any of the embodiments of the invention. Applicants additionally reserve the right to exclude any metabolic-related disorder from any of the embodiments of the invention.

Other uses of the disclosed receptors and methods will become apparent to those in the art based upon, inter alia, a review of this patent document.

The following examples are given to illustrate the invention and are not intended to be inclusive in any manner:

EXAMPLES

The examples are provided to further define the invention without, however, limiting the invention to the specifics of these examples.

Example 1

Affymetrix Chip Analysis of Mouse GPR43 Expression in Mouse Adult and Fetal Tissues and Cells In this example, the expression level of mouse GPR43 was determined in several mouse adult and fetal tissues and cells using an Affymetrix gene chip (from left to right: fetal brain, pons spinal cord, spinal cord lower, SN pons thalamus, olfactory bulb, thalamus, hippocampus, swiss-3T3, 3T3-LI adipocyte, BV2+LPS 24 hr, NIH-3T3, 3T3-LI preadipocvte, NIT-1, N1E-115 differentiated, E14TG2A, BV2, N1E-115, BV2+ LPS 4 hr, NIT CTL, C57BL6 ES, D3 ES, lymph node, bone marrow, T-cells, CD4+ ovalbumin, spleen, T-cells, CD4+ naive, *thymus*, duodenum, skin fat, brown fat, epididimal fat, ventricle, atria, aorta, fibroblast, neonatal cardiac, ventricular myocytes, hypoxia-reoxyg, neonatal, ventricular myocytes, normoxia, neonatal, ventricular myocytes, ventricular myocytes, hypoxia, neonatal, ventricle, left TAC, ventricle, left sham, large intestine proximal, stomach fondues, small intestine, large intestine distal, stomach antrum, white blood cells, liver, lung, trachea, salivary gland, bone, fibroblast, dermal, adrenal gland, skeletal muscle, skin, bladder, skin, mouth, oral mucosa, mouth, epidermis, betaTC6, beta islets, C57B1/ 6, alpha TC9, beta islets, db/db, uterus, umbilical cord, ovary)

1. Affymetrix Genechip® Technology

Nucleotide sequences corresponding to several G protein-coupled receptors (GPCRs) were submitted to Affymetrix. Affymetrix designed and manufactured an oligonucleotide microarray for the purpose of measuring mRNA expression levels of these receptors in various tissues via its GeneChip® Technology. RNA samples from a large number of tissue and cell types were amplified, labeled, hybridized to the microarray, and data analyzed according to manufacturer's instructions.

GPCRs were determined to be expressed if the expression index was greater than 50 (based upon and according to manufacturer's instructions). The data was analyzed and had indicated that classification of GPCRs with an expression index greater than 50 was reasonable because a number of known GPCRs had previously been reported to be expressed in neuronal tissues with an expression index greater than 50.

Using the GeneChip®, Applicant has discovered GPR43 has high levels of expression in fat, large intestine, pancreatic islets and islet cell lines and 3T3 adipocytes (see FIG. 1).

Example 2

RT-PCR Analysis of GPR43 Expression in Human and Mouse Tissues and Cells

Figure 2:
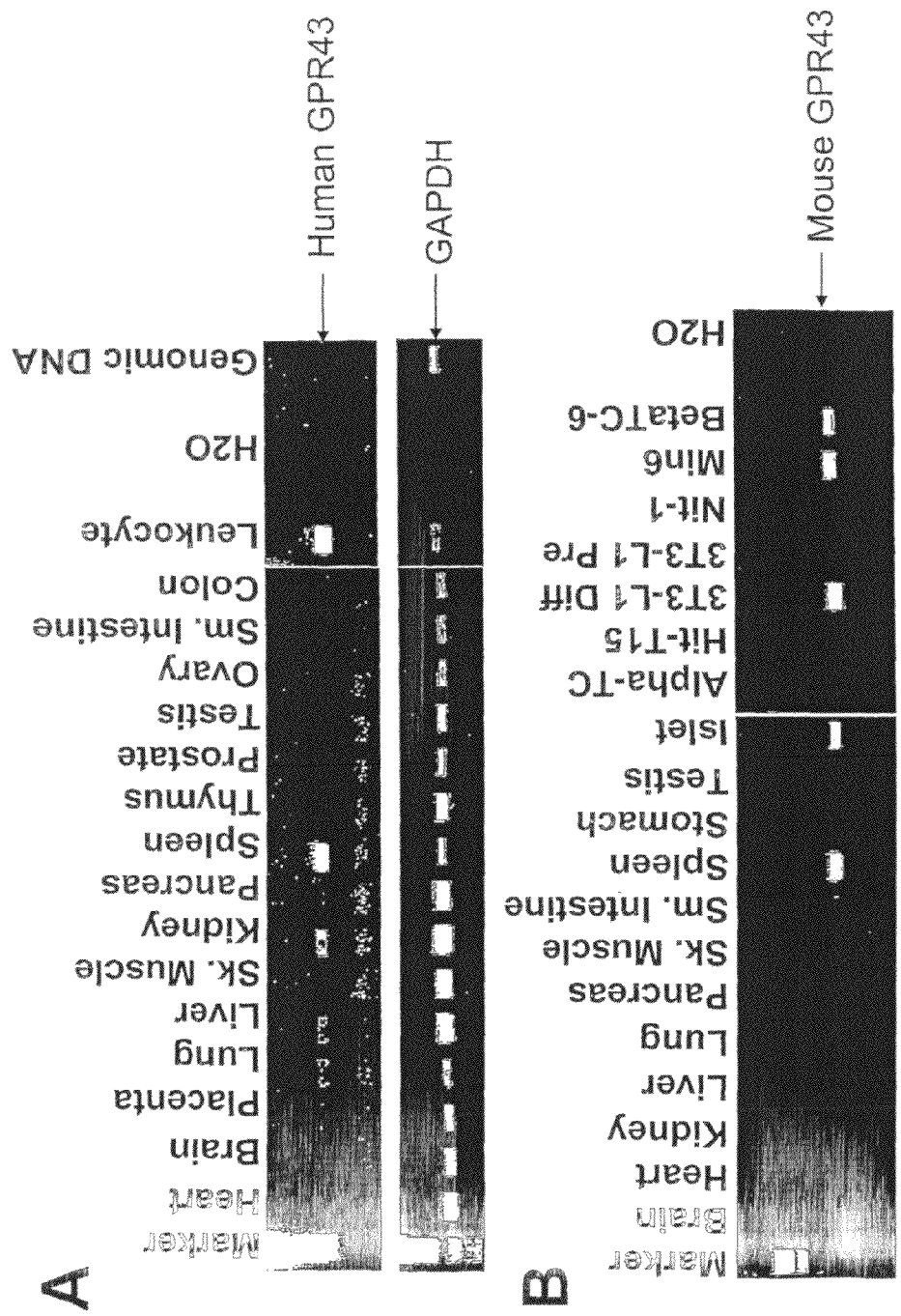
FIG. 2 shows RT-PCR analysis of human GPR43 expression in selected human tissues and cells (top panel) and mouse GPR43 expression in selected mouse tissues, cells and cell lines (bottom panel).

In this example, the expression level of human and mouse GPR43 was determined in several human and mouse tissues and cell types using an RT-PCR assay. As shown in FIG. 2, top panel, human GPR43 gene expression was observed in several human tissues and cells including, for example, placenta lung, liver, kidney, pancreas, spleen, prostate and leukocytes. In addition, as shown in FIG. 2, bottom panel, mouse GPR43 gene expression was observed in several mouse tissues, cells and cell lines, including, for example, lung, pancreas, skeletal muscle, small intestine, spleen, stomach, islets 3T3-L1 differentiated adipocytes, Nit-1 cells, Min6 cells and beta TC-6 cells.

For this experiment, human cDNAs were obtained from Human MTC Panel I and Human MTC Panel II (Clontech). Mouse Poly A+RNAs were obtained from Clontech. Subsequently, cDNAs were synthesized with iScript cDNA Synthesis Kit (Bio-Rad) according to the manufacturer's protocol. For the reaction 1 µl of 1:10 diluted mouse Poly A+, 8 µl of 5×iScript Reaction Mix and 2 µl of iScript Reverse Transcriptase along with water were assembled into a total volume of 40 µl. The reaction were run in PCR machine at 25° C., 5 min; 42° C., 30 min; 85° C., 5 min.

Cell lines RNAs and mouse islet RNA were isolated using Trizol, and were further treated with DNAse using DNA-free kit (Ambion) according to the manufacturer's protocol. Tug of DNase treated RNA was used in a 40 µl total reaction volume using iScript cDNA Synthesis Kit (Bio-Rad).

PCR reactions for human and mouse GPR43 were performed with Invitrogen's Platinum PCR Supermix. For each reaction, 2 µl of cDNA, 48 µl of Supermix, 0.2 µl of each primer (100 µM stock) were assembled in a volume of 50 µl total. The reaction for human GPR43 were performed in the PCR machine at 95° C., 4 min denature, followed by 30 cycles of 95° C., 1 min; 60° C., 30 sec; 72° C., 1 min, finally ended with the extension at 72° C. for 7 minutes. The annealing temperature used for mouse GPR35 was 63° C.

G3PDH 5' and 3' PCR primers were provided as a control by Clontech in Human MTC Panel I and II. For G3PDH PCR reaction, 2 µl of cDNA, 45 µl of Platinum PCR Supermix (Invitrogen), 1 µl of each primer (10 µm stock) were assembled in a volume of 50 µl total. The reaction was performed in the PCR machine at 95° C., 1 min denature, followed by 23 cycles of 95° C., 30 sec; 68° C., 3 min, finally ended with extension at 68° C. for 3 minutes.

```
Human GPR43 RT-PCR primer pairs:
Forward:
5'-GTCTGGTGGCCTGGGTTATGTCCT-3'      (SEQ ID NO: 3)

Reverse:
5'-CCTGCGCACCAGTGAAGAAGAGAA-3'      (SEQ ID NO: 4)

Mouse GPR43 RT-PCR primer pairs:
Forward:
5'-GTTATCCCGCCGGCCACTGTATG-3'       (SEQ ID NO: 5)

Reverse:
5'-GCGCACCACGGAGGAGGAGAAG-3'        (SEQ ID NO: 6)
```

Example 3

Identification of GPR43 Modulators

In this example, GPR43 modulators are identified using a screening protocol in melanophores.

1. Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, which bind to and/or activate GPCRs. This method can be conducted by introducing test cells of a pigment cell line capable of dispersing or aggregating their pigment in response to a specific stimulus and expressing an exogenous clone coding for the GPCR. An initial state of pigment disposition can be set using, for example, using melatonin, MSH or light. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods were followed according to the disclosure of U.S. Pat. No. 5,462,856 and U.S. Pat. No. 6,051,386. These patent disclosures are hereby incorporated by reference in their entirety.

Melanophores are transfected by electroporation with a plasmid which contains the coding sequence of mouse or human GPR43. The cells are plated in 96-well plates. 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7× L-15 (Gibco). After one hour, the cells in serum-free media remain in a pigment-dispersed state while the melatonin-treated cells are in a pigment-aggregated state. At this point, the cells are treated with different compounds from a proprietary compound library containing 140,000-150,000 organic small molecule compounds. If GPR43 bound to the compound, the melanophores would be expected to undergo a color change, for example, due to pigment aggregation, in response to the compound.

Example 4

Oral Glucose Tolerance Test

A GPR43 modulator such as an agonist, antagonist or inverse agonist can be tested for its effect on plasma glucose after oral glucose administration.

For example, male C57bl/6 mice at age 67 days can be fasted for 18 hours and randomly grouped to receive a GPR43 modulator at selected doses, or vehicle (PET which contains 80% PEG, 10% Tween80, and 10% Ethanol). The GPR43 modulator is delivered orally via a gavage needle (p.o. volume at 100 µl). Thirty minutes after administration of the GPR43 modulator or vehicle, mice are administered orally with dextrose at 3 g/kg dose. Levels of blood glucose are determined at the several time points using Glucometer Elite XL (Bayer).

Glucose tolerance can also be tested using i.p. delivery of glucose. For example, 68 day old male C57B1/6 mice are treated with a GPR43 modulator at 100 mg/kg or with PET vehicle after 18 hours of fasting. Thirty minutes after administration of the GPR43 modulator or vehicle, mice are administered i.p. with dextrose at 2 g/kg dose. Levels of blood glucose are determined at the selected time points using Glucometer Elite XL (Bayer).

Example 5

Insulin-Stimulated Glucose Uptake in 3T3-L1 Adipocytes

In this example, the effect of GPR43 modulators on insulin-stimulated glucose uptake in adipocytes is tested using a $^3$H-2-deoxyglucose uptake assay.

Briefly, 3T3-L1 cells are first differentiated into adipoctyes using a standard protocol (Patel and Lane, *Proc. Natl. Acad. Sci. U.S.A.* 96:1279-1284 (1999). Cells are then stimulated for three hours with serum-free medium containing either vehicle or 5 µM of a GPR43 modulator. Cells are then washed twice in Krebs-Ringer phosphate buffer and incubated in Krebs-Ringer phosphate buffer for 20 minutes in the presence or absence of 10 nM insulin. 2-deoxyglucose transport is measured by adding 0.05 mM (0.5 µCi/mol)$^3$H-2-deoxyglucose and 0.05 mM cold 2-deoxyglucose to the cells for 5 minutes at 37° C. To terminate the transport reaction, the cells are washed three times with ice-cold PBS and solubilized in 1% Triton-X. The level of radioactivity in the lysates is determined by scintillation counting.

Example 6

Assays for Determination of GPCR Activation

A variety of approaches are available for assessment of activation of human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to endogenous GPCRs and non-endogenous, constitutively activated GPCRs. The assay is generic and has application to drug discovery at all G protein-coupled receptors.

The [$^{35}$S]GTPγS assay is incubated in 20 mM HEPES and between 1 and about 20 mM MgCl$_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 µg membrane protein (e.g., 293 cells expressing the GPR43; this amount can be adjusted for optimization) and 10 µm GDP (this amount can be changed for optimization) for 1 hour. Wheatgerm agglutinin beads (25 µl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express a receptor.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 minutes. The cell pellet is carefully re-suspended into an appropriate volume of PBS (about 3 ml/plate). The cells are then counted using a hemocytometer and additional PBS is added to give the appropriate number of cells (with a final volume of about 50 µl/well).

cAMP standards and Detection Buffer (comprising 1 µCi of tracer [$^{125}$I] cAMP (50 µl) to 11 ml Detection Buffer) is prepared and maintained in accordance with the manufacturer's instructions. Assay Buffer is prepared fresh for screening and contains 50 µl of Stimulation Buffer, 3 µl of candidate compound (12 µM final assay concentration) and 50 µl cells. Assay Buffer is stored on ice until utilized. The assay, preferably carried out, for example, in a 96-well plate, is initiated by addition of 50 µl of cAMP standards to appropriate wells followed by addition of 50 µl of PBSA to wells H11 and H12. 50 µl of Stimulation Buffer is added to all wells. DMSO (or selected candidate compounds) is added to appropriate wells using a pin tool capable of dispensing 3 µl of compound solution, with a final assay concentration of 12 µM candidate compound and 100 µl total assay volume. The cells are then added to the wells and incubated for 60 minutes at room temperature. 100 µl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP for Gi Coupled Target GPCRs

TSHR is a Gs coupled GPCR that causes the accumulation of cAMP upon activation. TSHR can be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of activation of a Gi coupled receptor can be accomplished by co-transfecting, non-endogenous, constitutively activated TSHR (TSHR-A623I) (or an endogenous, constitutively active Gs coupled receptor) as a "signal enhancer" with a Gi linked target GPCR to establish a baseline level of cAMP. Upon creating an endogenous or non-endogenous version of the Gi coupled receptor, the target GPCR is then co-transfected with the signal enhancer, and it is this material that can be used for screening. In some embodiments, this approach is preferably used in the direct identification of candidate compounds against Gi coupled receptors. It is noted that for a Gi coupled GPCR, when this approach is used, an inverse agonist of the target GPCR will increase the cAMP signal and an agonist will decrease the cAMP signal.

On day one, 2×10$^4$ 293 cells/well are plated out. On day two, two reaction tubes are prepared (the proportions to follow for each tube are per plate): tube A is prepared by mixing 2 µg DNA of each receptor transfected into the mammalian cells, for a total of 4 µg DNA (e.g., pCMV vector; pCMV vector with mutated THSR (TSHR-A623I); TSHR-A623I and GPCR, etc.) in 1.2 ml serum free DMEM (Irvine Scientific, Irvine, Calif.); tube B is prepared by mixing 120 µl lipofectamine (Gibco BRL) in 1.2 ml serum free DMEM. Tubes A and B are then admixed by inversions (several times), followed by incubation at room temperature for 30-45 minutes. The admixture is referred to as the "transfection mixture". Plated 293 cells are washed with 1XPBS, followed by addition of 10 ml serum free DMEM. 2.4 ml of the transfection mixture is then added to the cells, followed by incubation for 4 hours at 37° C./5% $CO_2$. The transfection mixture is then removed by aspiration, followed by the addition of 25 ml of DMEM/10% Fetal Bovine Serum. Cells are then incubated at 37° C./5% $CO_2$. After 24 hours incubation, cells are harvested and utilized for analysis.

A Flash Plate™ Adenylyl Cyclase kit (New England Nuclear; Cat. No. SMP004A) is designed for cell-based assays, but can be modified for use with crude plasma membranes depending on the need of the skilled artisan. The Flash Plate wells contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express a receptor of interest.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS is added to each plate. Cells are pipetted off the plate and the cell suspension is collected into a 50 ml conical centrifuge tube. Cells are then centrifuged at room temperature at 1,100 rpm for 5 minutes. The cell pellet is carefully re-suspended into an appropriate volume of PBS (about 3 ml/plate). The cells are then counted using a hemocytometer and additional PBS is added to give the appropriate number of cells (with a final volume of about 50 μl/well).

cAMP standards and Detection Buffer (comprising 1 μCi of tracer [$^{125}$I] cAMP (50 μl) to 1 ml Detection Buffer) is prepared and maintained in accordance with the manufacturer's instructions. Assay Buffer should be prepared fresh for screening and contain 50 μl of Stimulation Buffer, 3 μl of candidate compound (12 μM final assay concentration) and 50 μl cells. Assay Buffer can be stored on ice until utilized. The assay can be initiated by addition of 50 μl of cAMP standards to appropriate wells followed by addition of 50 μl of PBSA to wells H-11 and H12. Fifty μl of Stimulation Buffer is added to all wells. Selected compounds (e.g., TSH) are added to appropriate wells using a pin tool capable of dispensing 3 μl of compound solution, with a final assay concentration of 12 μM candidate compound and 100 μl total assay volume. The cells are then added to the wells and incubated for 60 minutes at room temperature. 100 μl of Detection Mix containing tracer cAMP is then added to the wells. Plates are then incubated additional 2 hours followed by counting in a Wallac MicroBeta scintillation counter. Values of cAMP/well are extrapolated from a standard cAMP curve which is contained within each assay plate.

4. Reporter-Based Assays a. CRE-LUC Reporter Assay (Gs-Associated Receptors)

293 or 293T cells are plated-out on 96 well plates at a density of 2×10$^4$ cells per well and are transfected using Lipofectamine Reagent (BRL) the following day according to manufacturer instructions. A DNA/lipid mixture is prepared for each 6-well transfection as follows: 260 ng of plasmid DNA in 100 μl of DMEM is gently mixed with 2 μl of lipid in 100 μl of DMEM (the 260 ng of plasmid DNA consists of 200 ng of a 8xCRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8XCRE-Luc reporter plasmid is prepared as follows: vector SRIF-β-gal is obtained by cloning the rat somatostatin promoter (−71/+51) at BglV-HindIII site in the pβgal-Basic Vector (Clontech). Eight (8) copies of cAMP response element are obtained by PCR from an adenovirus template AdpCF126CCRE8 (see, Suzuki et al., Hum Gene Ther 7:1883-1893 (1996); the disclosure of which is hereby incorporated by reference in its entirety) and cloned into the SRIF-β-gal vector at the Kpn-BglV site, resulting in the 8xCRE-β-gal reporter vector. The 8xCRE-Luc reporter plasmid is generated by replacing the beta-galactosidase gene in the 8xCRE-β-gal reporter vector with the luciferase gene obtained from the pGL3-basic vector (Promega) at the HindIII-BamHI site. Following 30 minutes incubation at room temperature, the DNA/lipid mixture is diluted with 400 μl of DMEM and 100 μl of the diluted mixture is added to each well. 100 μl of DMEM with 10% FCS are added to each well after a four hour incubation in a cell culture incubator. The following day the transfected cells are changed with 200 μl/well of DMEM with 10% FCS. Eight (8) hours later, the wells are changed to 100 μl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue No. 219073) can be utilized following the protocol set forth above with respect to the CREB reporter assay, except that the components of the calcium phosphate precipitate are 410 ng pAP1-Luc, 80 ng pCMV-receptor expression plasmid, and 20 ng CMV-SEAP.

c. SRF-LUC Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, for example, COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate and kept on the cells in a serum free media for 24 hours. The last 5 hours the cells are incubated with, for example, 1 μM, candidate compound. Cells are then lysed and assayed for luciferase activity using a Luclite™ Kit (Packard, Cat. No. 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular IP3 Accumulation Assay (Gq-Associated Receptors)

On day 1, cells comprising the receptor of interest (endogenous or non-endogenous) can be plated onto 24 well plates, usually 1×10$^5$ cells/well (although this number can be optimized). On day 2 cells can be transfected by first mixing 0.25 μg DNA in 50 μl serum free DMEM/well and 2 μl lipofectamine in 50 μl serum free DMEM/well. The solutions are gently mixed and incubated for 15-30 minutes at room temperature. Cells are washed with 0.5 ml PBS and 400 µl of serum free media is mixed with the transfection media and added to the cells. The cells are then incubated for 3-4 hours at 37° C./5% $CO_2$ and then the transfection media is removed and replaced with 1 ml/well of regular growth media. On day 3 the cells are labeled with $^3H$-myo-inositol. Briefly, the media is removed and the cells are washed with 0.5 ml PBS. Then 0.5 ml inositol-free/serum free media (GIBCO BRL) is added/well with 0.25 µCi of $^3H$-myo-inositol/well and the cells are incubated for 16-18 hours overnight at 37° C./5% $CO_2$. On Day 4 the cells are washed with 0.5 ml PBS and 0.45 ml of assay medium is added containing inositol-free/serum free media, 10 µM pargyline, 10 mM lithium chloride or 0.4 ml of assay medium and 50 µl of 10× ketanserin (ket) to final concentration of 10 µM, if using a control construct containing a serotonin receptor. The cells are then incubated for 30 minutes at 37° C. The cells are then washed with 0.5 ml PBS and 200 µl of fresh/ice cold stop solution (1M KOH; 18 mM Na-borate; 3.8 mM EDTA) is added/well. The solution is kept on ice for 5-10 minutes or until cells were lysed and then neutralized by 200 µl of fresh/ice cold neutralization sol. (7.5% HCL). The lysate is then transferred into 1.5 ml eppendorf tubes and 1 ml of chloroform/methanol (1:2) is added/tube. The solution is vortexed for 15 seconds and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol Iris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 7

Fusion Protein Preparation a. GPCR:Gs Fusion Constuct

The design of the GPCR-G protein fusion construct can be accomplished as follows: both the 5' and 3' ends of the rat G protein Gsα (long form; Itoh, H. et al., *Proc. Natl. Acad. Sci.* 83:3776 (1986)) are engineered to include a HindIII sequence thereon. Following confirmation of the correct sequence (including the flanking HindIII sequences), the entire sequence is shuttled into pcDNA3.1(−) (Invitrogen, cat. no. V795-20) by subcloning using the HindIII restriction site of that vector. The correct orientation for the Gsα sequence is determined after subcloning into pcDNA3.1(−). The modified pcDNA3.1 (−) containing the rat Gsα gene at HindIII sequence is then verified; this vector is now available as a "universal" Gsα protein vector. The pcDNA3.1(−) vector contains a variety of well-known restriction sites upstream of the HindIII site, thus beneficially providing the ability to insert, upstream of the Gs protein, the coding sequence of a receptor of interest. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 Amino Acid Deletion)/Gi Fusion Construct

The design of a Gq(del)/Gi fusion construct can be accomplished as follows: the N-terminal six (6) amino acids (amino acids 2 through 7, having the sequence of TLESIM (SEQ ID NO:7)) of Gαq-subunit is deleted and the C-terminal five (5) amino acids having the sequence EYNLV (SEQ ID NO:8) is replaced with the corresponding amino acids of the Gαi Protein, having the sequence DCGLF (SEQ ID NO:9). This fusion construct can be obtained by PCR using the following primers:

```
                                      (SEQ ID NO: 10)
5'-gatcAAGCTTCCATGGCGTGCTGCCTGAGCGAGGAG-3'
and
                                      (SEQ ID NO: 11)
5'gatcGGATCCTTAGAACAGGCCGCAGTCCTTCAGGTTCAGCTGCAGGA

TGGTG-3'
``` and Plasmid 63313 which contains the mouse Gαq-wild type version with a hemagglutinin tag as template. Nucleotides in lower caps are included as spacers.

TaqPlus Precision DNA polymerase (Stratagene) can be utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product can be cloned into a pCRII-TOPO vector (Invitrogen) and sequenced using the ABI Big Dye Terminator kit (P.E. Biosystems). Inserts from a TOPO clone containing the sequence of the fusion construct can be shuttled into the expression vector pcDNA3.1(+) at the HindIII/BamHI site by a 2 step cloning process. Also see, PCT Application Number PCT/US02/05625 published as WO02068600 on 6 Sep. 2002, the disclosure of which is hereby incorporated by reference in its entirety.

Example 8

[$^{35}S$]GTPγS Assay

A. Membrane Preparation

In some embodiments membranes comprising the Target GPCR of interest for use in the identification of candidate compounds as, e.g., agonists, inverse agonists or antagonists, are prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials are kept on ice throughout the procedure. Firstly, the media is aspirated from a confluent monolayer of cells, followed by rinsing with 10 ml cold PBS, followed by aspiration. Thereafter, 5 ml of Membrane Scrape Buffer is added to scrape cells; this is followed by transfer of cellular extract into 50 ml centrifuge tubes (centrifuged at 20,000 rpm for 17 minutes at 4° C.). Thereafter, the supernatant is aspirated and the pellet is resuspended in 30 ml Membrane Wash Buffer followed by centrifuge at 20,000 rpm for 17 minutes at 4° C. The supernatant is then aspirated and the pellet resuspended in Binding Buffer. This is then homogenized using a Brinkman Polytron™ homogenizer (15-20 second bursts until the all material is in suspension). This is referred to herein as "Membrane Protein".

Bradford Protein Assay

Following the homogenization, protein concentration of the membranes is determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard is utilized, following manufacturer instructions (Biorad, cat. no. 500-0006).

b. Procedure

Duplicate tubes are prepared, one including the membrane, and one as a control "blank". Each tube contains 800 µl Binding Buffer. Thereafter, 10 µl of Bradford Protein Standard (1 mg/ml) is added to each tube, and 10 µl of membrane Protein is then added to just one tube (not the blank). Thereafter, 200 µl of Bradford Dye Reagent is added to each tube, followed by vortexing of each tube. After five (5) minutes, the tubes are re-vortexed and the material therein is transferred to cuvettes. The cuvettes are read using a CECIL 3041 spectrophotometer, at wavelength 595.

Identification Assay a. Materials

GDP Buffer consists of 37.5 ml Binding Buffer and 2 mg GDP (Sigma, cat. no. G-7127), followed by a series of dilutions in Binding Buffer to obtain 0.2 µM GDP (final concentration of GDP in each well is 0.1 µM GDP); each well comprising a candidate compound has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

b. Procedure

Candidate compounds can be screened using a 96-well plate format (these can be frozen at −80° C.). Membrane Protein (or membranes with expression vector excluding the Target GPCR, as control), are homogenized briefly until in suspension. Protein concentration is be determined using the Bradford Protein Assay set forth above. Membrane Protein (and control) is diluted to 0.25 mg/ml in Binding Buffer (final assay concentration, 12.5 µl g/well). Thereafter, 100 µl GDP Buffer is added to each well of a Wallac Scintistrip™ (Wallac). A 5 µl pin-tool is used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein is added to each well (a control well comprising membranes without the Target GPCR is also utilized), and pre-incubated for 5-10 minutes at room temperature. Thereafter, 50 µl of [$^{35}$S]GTPγS (0.6 nM) in Binding Buffer is added to each well, followed by incubation on a shaker for 60 minutes at room temperature (plates are covered with foil). The assay is then stopped by spinning of the plates at 4000 RPM for 15 minutes at 22° C. The plates are aspirated with an 8 channel manifold and sealed with plate covers. The plates are read on a Wallac 1450 using setting "Prot. #37" (as per manufacturer's instructions).

Example 9

Cyclic AMP Assay

Another assay approach for identifying candidate compounds as, e.g., agonists, inverse agonist, or antagonists, can be accomplished by utilizing a cyclase-based assay. In addition to direct identification, this assay approach can be utilized as an independent approach to provide confirmation of the results from the [$^{35}$S]GTPγS approach as set forth in the above example.

A modified Flash Plate™ Adenylyl Cyclase kit (New England Nuclear; Cat. No. SMP004A) can be utilized for direct identification of candidate compounds as inverse agonists and agonists to a receptor of interest in accordance with the following protocol.

Transfected cells are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 µCi of tracer [$^{125}$I]cAMP (100 µl) to 11 ml Detection Buffer] are prepared and maintained in accordance with the manufacturer's instructions. Assay Buffer is prepared fresh for screening and contains 20 mM HEPES, pH 7.4, 10 mM MgCl$_2$, 20 mM phospocreatine (Sigma), 0.1 units/nil creatine phosphokinase (Sigma), 50 µM GTP (Sigma), and 0.2 mM ATP (Sigma); Assay Buffer is then stored on ice until utilized.

Candidate compounds are added to, for example, 96-well plate wells (3 µl/well; 12 µM final assay concentration), together with 40 µl Membrane Protein (30 µg/well) and 50 µl of Assay Buffer. This admixture is then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

Example 10

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at 5.5×10$^4$ cells/well with complete culture medium (DMEM with 10% FBS, 2 mM L-glutamine, 1 mM sodium pyruvate) for assay the next day. Since GPR43 is coupled to Gαq, a promiscuous G protein such as Gα15, Gα16, or the chimeric Gq/Gi alpha subunit is not required in order to cause a detectable calcium flux. To prepare Fluo4-AM (Molecular Probe, #F14202) incubation buffer stock, 1 mg Fluo4-AM is dissolved in 467 µl DMSO and 467 µl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 µl of 4 µM Fluo4-AM/ 2.5 mM Probenicid (Sigma, #P8761)/20 mM HEPES/complete medium at pH 7.4. Incubation at 37° C./5% $CO_2$ is allowed to proceed for 60 minutes.

After the 1 hour incubation, the Fluo4-AM incubation buffer is removed and the cells are washed 2× with 100 µl wash buffer. In each well is left 100 µl wash buffer. The plate is returned to the incubator at 37° C./5% $CO_2$ for 60 minutes.

FLIPR (Fluorometric Imaging Plate Reader; Molecular Device) is programmed to add 50 µl candidate compound on the 30th second and to record transient changes in intracellular calcium concentration ([Ca2+]) evoked by the candidate compound for another 150 seconds. Total fluorescence change counts are used to determine agonist activity using the FLIPR software. The instrument software normalizes the fluorescent reading to give equivalent initial readings at zero.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example 11

MAP Kinase Assay

MAP kinase (mitogen activated kinase) can be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the candidate compound and then extracted with Laemmli buffer. The soluble fraction is applied to an SDS-PAGE gel and proteins are transferred electrophoretically to nitrocellulose or Immobilin. Immunoreactive bands are detected by standard Western blotting technique. Visible or chemiluminescent signals are recorded on film and can be quantified by densitometry.

Another approach is based on evaluation of the MAP kinase activity via a phosphorylation assay. Cells are stimulated with the candidate compound and a soluble extract is prepared. The extract is incubated at 30° C. for 10 minutes with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic proein bound by streptavidin to a filter support. The myelin basic protein is a substrate for activated MAP kinase. The phosphorylation reaction is carried out for 10 minutes at 30° C. The extract can then be aspirated through the filter, which retains, the phosphorylated myelin basic protein. The filter is washed and counted for $^{32}$P by liquid scintillation counting.

Example 12

Receptor Binding Assay

In addition to the methods described herein, another means for evaluating a candidate compound is by determining binding affinities to the GPR43 receptor. This type of assay generally requires a radiolabelled ligand to the GPR43 receptor. In addtion to the use of known ligands for the GPR43 receptor and radiolabels thereof, GPR43 agonist compounds can be labelled with a radioisotope and used in an assay for evaluating the affinity of a candidate compound to the GPR43 receptor.

A radiolabelled GPR43 compound such as a GPR43 agonist can be used in a screening assay to identify/evaluate compounds. In general terms, a newly synthesized or identified compound (i.e., candidate compound) can be evaluated for its ability to reduce binding of the radiolabelled GPR43 agonist to the GPR43 receptor. Accordingly, the ability to compete with the radiolabelled GPR43 agonist for the binding to the GPR43 receptor directly correlates to the binding affinity of the candidate compound to the GPR43 receptor.

Assay Protocol for Determining Receptor Binding for GPR43:

A. GPR43 Receptor Preparation

For example, HEK293 cells (human kidney, ATCC) can be transiently or stably transfected with GPR43 as described herein. For example, 293 cells can be transiently transfected with 10 µg human GPR43 receptor and 60 µl Lipofectamine (per 15-cm dish), and grown in the dish for 24 hours (75% confluency) with a media change. Cells are removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50– ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) is added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 µl of appropriately diluted membranes (diluted in assay buffer containing 50 mM Tris HCl (pH 7.4), 10 mM $MgCl_2$, and 1 mM EDTA; 5-50 µg protein) is added to 96-well polyproylene microtiter plates followed by addition of 100 µl of assay buffer and 50 µl of radiolabelled GPR43 agonist. For nonspecific binding, 50 µl of assay buffer is added instead of 100 µl and an additional 50 µl of 10 µM cold GPR43 is added before 50 µl of radiolabelled GPR43 agonist is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plates are sealed, 50 µl of Optiphase Supermix is added to each well, the top of the plates are sealed, and plates are counted in a Trilux MicroBeta scintillation counter. For compound competition studies, instead of adding 100 µl of assay buffer, 100 µl of appropriately diluted candidate compound is added to appropriate wells followed by addition of 50 μl of radiolabelled GPR43 agonist.

C. Calculations

The candidate compounds are initially assayed at 1 and 0.1 μM and then at a range of concentrations chosen such that the middle dose would cause about 50% inhibition of a radiolabelled GPR43 agonist binding (i.e., $IC_{50}$). Specific binding in the absence of candidate compound ($B_O$) is the difference of total binding ($B_T$) minus non-specific binding (NSB) and similarly specific binding (in the presence of candidate compound) (B) is the difference of displacement binding ($B_D$) minus non-specific binding (NSB). $IC_{50}$ is determined from an inhibition response curve, logit-log plot of % $B/B_O$ vs concentration of candidate compound.

$K_i$ is calculated by the Cheng and Prustoff transformation:

$$K_i = IC_{50}/(1+[L]/K_D)$$

where [L] is the concentration of a radiolabelled GPR43 agonist used in the assay and $K_D$ is the dissociation constant of a radiolabelled GPR43 agonist determined independently under the same binding conditions.

Example 13

Rodent Diabetes Model

Rodent models of type II diabetes associated with obesity and insulin resistance have been developed. Genetic models such as db/db and ob/ob [see Diabetes (1982) 31:1-6] in mice and fa/fa in zucker rats have been developed for understanding the pathophysiology of disease and for testing candidate therapeutic compounds [Diabetes (1983) 32:830-838; Arum Rep Sankyo Res Lab (1994) 46:1-57]. The homozygous animals, C57 BL/KsJ-db/db mice developed by Jackson Laboratory are obese, hyperglycemic, hyperinsulinemic and insulin resistant [J Clin Invest (1990) 85:962-967], whereas heterozygotes are lean and normoglycemic. In the db/db model, mice progressively develop insulinopenia with age, a feature commonly observed in late stages of human type II diabetes when sugar levels are insufficiently controlled. Since this model resembles that of human type II diabetes, the metabolic stabilizing compounds of the present invention are tested for activities including, but not limited to, lowering of plasma glucose and triglycerides. Zucker (fa/fa) rats are severely obese, hyperinsulinemic, and insulin resistant {Coleman, Diabetes (1982) 31:1; E Shafrir in Diabetes Mellitus, H Rifkin and D Porte, Jr, Eds [Elsevier Science Publishing Co, New York, ed. 4, (1990), pp. 299-340]}, and the fa/fa mutation may be the rat equivalent of the murine db mutation [Friedman et al, Cell (1992) 69:217-220; Truett et al, Proc Natl Acad Sci USA (1991) 88:7806]. Tubby (tub/tub) mice are characterized by obesity, moderate insulin resistance and hyperinsulinemia without significant hyperglycemia [Coleman et al, Heredity (1990) 81:424].

The present invention encompasses the use of compounds of the invention for reducing the insulin resistance and hyperglycemia in any or all of the above rodent diabetes models, in humans with type II diabetes or other preferred metabolic-related disorders or disorders of lipid metabolism described previously, or in models based on other mammals. Plasma glucose and insulin levels can be tested, as well as other factors including, but not limited to, plasma free fatty acids and triglycerides.

In Vivo Assay for Anti-Hyperglycemic Activity of Compounds of the Invention

Genetically altered obese diabetic mice (db/db) (male, 7-9 weeks old) are housed (7-9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of several mice that are distributed so that the mean glucose levels are equivalent in each group at the start of the study. db/db mice are dosed by micro-osmotic pumps, inserted using isoflurane anesthesia, to provide compounds of the invention, saline, or an irrelevant compound to the mice subcutaneously (s.c.). Blood is sampled from the tail vein at intervals thereafter and analyzed for blood glucose concentrations. Significant differences between groups (comparing compounds of the invention to saline-treated) are evaluated using Student t-test.

The foregoing is provided by way of illustration and not limitation. Other illustrative rodent models for type II diabetes have been described [Moller D E, Nature (2001) 414: 821-7 and references therein; and Reed M J et al., Diabetes, Obesity and Metabolism (1999) 1:75-86 and reference therein; the disclosure of each of which is hereby incorporated by reference in its entirety].

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

---

We claim:

1. A method of screening for a compound that is useful in the treatment of insulin resistance, impaired glucose tolerance or diabetes, comprising:
    a) identifying a compound that decreases the activity of a GPCR, wherein said GPCR comprises an amino acid sequence that is at least 90% identical to SEQ ID NO: 2 and is capable of being activated by acetate or a short chain carboxylic acid; and,
    b) testing the compound identified in step a) to determine if said compound is useful in the treatment of insulin resistance, impaired glucose tolerance or diabetes, wherein the testing is done by administering the compound to a mammal and measuring blood glucose.

2. The method of claim 1, wherein said GPCR is human.

3. The method of claim 1, wherein the identifying step comprises a second messenger assay.

4. The method of claim 1, wherein said GPCR comprises an amino acid sequence that is at least 95% identical to SEQ ID NO: 2.

* * * * *

SEQUENCE LISTING

<160> NUMBER OF SEQ ID NOS: 11

<210> SEQ ID NO 1
<211> LENGTH: 993
<212> TYPE: DNA
<213> ORGANISM: Homo sapiens

<400> SEQUENCE: 1

```
atgctgccgg actggaagag ctccttgatc ctcatggctt acatcatcat cttcctcact      60
ggcctccctg ccaacctcct ggccctgcgg gcctttgtgg ggcggatccg ccagcccag      120 cctgcacctg tgcacatcct cctgctgagc ctgacgctgg ccgacctcct cctgctgctg      180
```

```
ctgctgccct tcaagatcat cgaggctgcg tcgaacttcc gctggtacct gcccaaggtc    240
gtctgcgccc tcacgagttt tggcttctac agcagcatct actgcagcac gtggctcctg    300
gcgggcatca gcatcgagcg ctacctggga gtggctttcc ccgtgcagta caagctctcc    360
cgccggcctc tgtatggagt gattgcagct ctggtggcct gggttatgtc ctttggtcac    420
tgcaccatcg tgatcatcgt tcaatacttg aacacgactg agcaggtcag aagtggcaat    480
gaaattacct gctacgagaa cttcaccgat aaccagttgg acgtggtgct gcccgtgcgg    540
ctggagctgt gcctggtgct cttcttcatc cccatggcag tcaccatctt ctgctactgg    600
cgttttgtgt ggatcatgct ctcccagccc cttgtggggg cccagaggcg cgccgagcc    660 gtggggctgg ctgtggtgac gctgctcaat ttcctggtgt gcttcggacc ttacaacgtg    720
tcccacctgg tggggtatca ccagagaaaa agcccctggt ggcggtcaat agccgtggtg    780
ttcagttcac tcaacgccag tctggacccc ctgctcttct atttctcttc ttcagtggtg    840
cgcagggcat ttgggagagg gctgcaggtg ctgcggaatc agggctcctc cctgttggga    900
cgcagaggca aagacacagc agagggaca aatgaggaca ggggtgtggg tcaaggagaa    960
gggatgccaa gttcggactt cactacagag tag                                 993
```

<210> SEQ ID NO 2
<211> LENGTH: 330
<212> TYPE: PRT
<213> ORGANISM: Homo sapiens
<400> SEQUENCE: 2

```
Met Leu Pro Asp Trp Lys Ser Ser Leu Ile Leu Met Ala Tyr Ile Ile
 1               5                  10                  15

Ile Phe Leu Thr Gly Leu Pro Ala Asn Leu Leu Ala Leu Arg Ala Phe
            20                  25                  30

Val Gly Arg Ile Arg Gln Pro Gln Pro Ala Pro Val His Ile Leu Leu
        35                  40                  45

Leu Ser Leu Thr Leu Ala Asp Leu Leu Leu Leu Leu Leu Pro Phe
    50                  55                  60

Lys Ile Ile Glu Ala Ala Ser Asn Phe Arg Trp Tyr Leu Pro Lys Val
65                  70                  75                  80

Val Cys Ala Leu Thr Ser Phe Gly Phe Tyr Ser Ser Ile Tyr Cys Ser
                85                  90                  95

Thr Trp Leu Leu Ala Gly Ile Ser Ile Glu Arg Tyr Leu Gly Val Ala
            100                 105                 110

Phe Pro Val Gln Tyr Lys Leu Ser Arg Arg Pro Leu Tyr Gly Val Ile
        115                 120                 125

Ala Ala Leu Val Ala Trp Val Met Ser Phe Gly His Cys Thr Ile Val
    130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Ala Val Gly Leu Ala
    210                 215                 220

Val Val Thr Leu Leu Asn Phe Leu Val Cys Phe Gly Pro Tyr Asn Val
```

```
            225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
                260                 265                 270

Phe Tyr Phe Ser Ser Val Val Arg Arg Ala Phe Gly Arg Gly Leu
            275                 280                 285

Gln Val Leu Arg Asn Gln Gly Ser Ser Leu Leu Gly Arg Arg Gly Lys
        290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ctctggtggc ctgggttatg tcct                                      24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
cctgcgcacc actgaagaag agaa                                      24

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gttatcccgc cggccactgt atg                                       23

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gcgcaccacg gaggaggaga ag                                        22

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 7

Thr Leu Glu Ser Ile Met
```

```
<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Glu Tyr Asn Leu Val
 1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Asp Cys Gly Leu Phe
 1               5

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
gatcaagctt ccatggcgtg ctgcctgagc gaggag                                   36

<210> SEQ ID NO 11
<211> LENGTH: 53
<212> TYPE: DNA
<213> ORGANISM: Artificial Sequence
<220> FEATURE:
<223> OTHER INFORMATION: Primer

<400> SEQUENCE: 11
gatcggatcc ttagaacagg ccgcagtcct tcaggttcag ctgcaggatg gtg               53
```